(12) United States Patent
Yang et al.

(10) Patent No.: US 10,421,949 B2
(45) Date of Patent: Sep. 24, 2019

(54) MICROCARRIER PERFUSION CULTURING METHODS AND USES THEREOF

(71) Applicant: Genzyme Corporation, Cambridge, MA (US)

(72) Inventors: Jianguo Yang, Sudbury, MA (US); Yang Yang, Hopkinton, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 14/769,783

(22) PCT Filed: Feb. 21, 2014

(86) PCT No.: PCT/US2014/017785
§ 371 (c)(1),
(2) Date: Aug. 21, 2015

(87) PCT Pub. No.: WO2014/130864
PCT Pub. Date: Aug. 28, 2014

(65) Prior Publication Data
US 2016/0017291 A1    Jan. 21, 2016

Related U.S. Application Data

(60) Provisional application No. 61/768,215, filed on Feb. 22, 2013.

(51) Int. Cl.
C12N 5/071 (2010.01)
C12N 5/00 (2006.01)
C12P 21/00 (2006.01)

(52) U.S. Cl.
CPC ......... *C12N 5/0682* (2013.01); *C12N 5/0075* (2013.01); *C12P 21/00* (2013.01); *C12N 2510/02* (2013.01); *C12N 2527/00* (2013.01); *C12N 2531/00* (2013.01)

(58) Field of Classification Search
CPC ............... C12N 5/0682; C12N 5/0075; C12N 2527/00; C12N 2510/02; C12N 2531/00
USPC ............................... 435/70.3, 352, 358, 403
See application file for complete search history.

(56) References Cited

U.S. PATENT DOCUMENTS

| | | |
|---|---|---|
| 4,522,811 A | 6/1985 | Eppestein et al. |
| 7,354,576 B2 | 4/2008 | Kakkis et al. |
| 9,909,101 B2 | 3/2018 | Yang et al. |
| 2003/0113915 A1 | 6/2003 | Heidemann et al. |
| 2005/0186669 A1 | 8/2005 | Ho et al. |
| 2008/0199958 A1 | 8/2008 | Hui |
| 2008/0206819 A1 | 8/2008 | Tsao et al. |
| 2009/0042253 A1 | 2/2009 | Hiller et al. |
| 2009/0233334 A1 | 9/2009 | Hildinger et al. |
| 2010/0076380 A1 | 3/2010 | Hui |
| 2011/0020929 A1 | 1/2011 | Schober et al. |
| 2011/0212493 A1 | 9/2011 | Hirschel |
| 2012/0164066 A1 | 6/2012 | Greene et al. |
| 2014/0154726 A1 | 6/2014 | Yang et al. |
| 2014/0255994 A1 | 9/2014 | Konstantinov et al. |
| 2014/0273206 A1 | 9/2014 | Jin et al. |
| 2015/0158907 A1 | 6/2015 | Zhou et al. |
| 2015/0183821 A1 | 7/2015 | Konstantinov et al. |
| 2015/0202595 A1 | 7/2015 | Godawat et al. |
| 2015/0203529 A1 | 7/2015 | Godawat et al. |
| 2015/0203531 A1 | 7/2015 | Godawat et al. |
| 2015/0203532 A1 | 7/2015 | Godawat et al. |
| 2015/0232505 A1 | 8/2015 | Konstantinov et al. |
| 2015/0353896 A1 | 12/2015 | Bruninghaus et al. |
| 2016/0002594 A1 | 1/2016 | Yang et al. |
| 2016/0017280 A1 | 1/2016 | Villiger-Oberbek et al. |
| 2016/0177361 A1 | 6/2016 | Bae et al. |

FOREIGN PATENT DOCUMENTS

| | | |
|---|---|---|
| CN | 1564863 | 1/2005 |
| CN | 104480897 | 4/2015 |
| WO | WO 2002/050251 | 6/2002 |
| WO | WO 2003/029442 | 4/2003 |
| WO | WO 03/039459 | 5/2003 |
| WO | WO 06/033935 | 3/2006 |
| WO | WO 06/138143 | 12/2006 |
| WO | WO 2006/039588 | 5/2007 |
| WO | WO 2008/073620 | 6/2008 |
| WO | WO 08/106515 | 9/2008 |
| WO | WO 09/034186 | 3/2009 |
| WO | WO 2008/127087 | 8/2012 |
| WO | WO 2012/078677 | 8/2012 |
| WO | WO 12/152945 | 11/2012 |
| WO | WO 13/116449 | 8/2013 |
| WO | WO 13/151616 | 10/2013 |
| WO | WO 14/066519 | 5/2014 |

(Continued)

OTHER PUBLICATIONS

Kim et al. Batch, Fed-Batch, and Microcarrier Cultures With CHO Cell Lines in a Pressure-Cycle Driven Miniturized Bioreactor; Biotechnology and Bioengineering; vol. 109, No. 1 (2011) pp. 137-145.*

De Jesus et al. Tubespin Satellites: A Fast Track Approach for Process Development With Animal Cells Using Shaking Technology; Biochemical Engineering Journal; vol. 17 (2004) pp. 217-223.*

Costa et al. The Impact of Microcarrier Culture Optimization on the Glycosylation Profile of a Monoclonal Antibody; SpringerPlus, vol. 2, No. 25 (Jan. 28, 2013) pp. 1-10.*

(Continued)

*Primary Examiner* — Sharmila G Landau
*Assistant Examiner* — Paul C Martin
(74) *Attorney, Agent, or Firm* — Fish & Richardson P.C.

(57) ABSTRACT

Provided herein are methods of culturing an adherent mammalian cell in a shake tube using a plurality of microcarriers and batch re-feed perfusion, and various methods that utilize these culturing methods.

21 Claims, 5 Drawing Sheets

(56) References Cited

FOREIGN PATENT DOCUMENTS

| | | |
|---|---|---|
| WO | WO 14/130872 | 8/2014 |
| WO | WO 2014/130864 | 8/2014 |
| WO | WO 2014/137903 | 9/2014 |
| WO | WO 2014/143691 | 9/2014 |
| WO | WO 2015/039115 | 3/2015 |
| WO | WO 2015/109146 | 7/2015 |
| WO | WO 2015/109151 | 7/2015 |
| WO | WO 15/188106 | 12/2015 |
| WO | WO 2015/188009 | 12/2015 |
| WO | WO 2015/191462 | 12/2015 |
| WO | WO 2016/106192 | 6/2016 |

OTHER PUBLICATIONS

Nam et al. The Effects of Microcarrier Culture on Recombinant CHO Cells Under Biphasic Hyperthermic Culture Conditions; Cytotechnology, vol. 59, pp. 81-91. (Year: 2009).*

Non-final Office Action issued in U.S. Appl. No. 14/061,657 dated Nov. 5, 2015, 12 pages.

U.S. Appl. No. 14/976,486, filed Dec. 21, 2015, Bae et al.

Barrett et al., "Microwell engineering characterization for mammalian cell culture process development," *Biotechnol Bioeng.*, 105(2):260-275, Feb. 1, 2010.

Chaturvedi et al., "Comparison of the behavior of CHO cells during cultivation in 24-square deep well microplates and conventional shake flask systems." *Biotechnology Reports.*, 1 (2014): 22-26.

Domansky et al., "Perfused multiwell plate for 3D liver tissue engineering," Lab on a Chip, 10(1):51-58 (Jan. 1, 2010).

Danielson et al., "Maximizing cell densities in miniprep-scale cultures with H15 medium and improved oxygen transfer," Biochemical Engineering J, 17:175-180, 2004.

Nam et al., "The effects of microcarrier culture on recombinant CHO cells under biphasic hypothermic culture conditions," *Cytotechnology*, 59(2):81-91, Epub May 2, 2009.

Rodrigues et al., "Technological progresses in monoclonal antibody production systems," *Biotechnol Prog.*, 26(2):332-351, Mar.-Apr. 2010.

Scott, "Growth of mesenchymal stromal cells in automated microwell cultures: influence of the engineering environment on cell growth kinetics and non-directed differentiation," (Doctoral dissertation, UCL (University College London), 202 pages, Sep. 2008.

Silk et al., "Fed-batch operation of an industrial cell culture process in shaken microwells," *Biotechnol Lett.*, 32(1):73-78, print Jan. 2010, Epub Sep. 17, 2009.

Strnad et al., "Optimization of cultivation conditions in spin tubes for Chinese hamster ovary cells producing erythropoietin and the comparison of glycosylation patterns in different cultivation vessels," Biotechnology Progress, 26(3):653-663 (2010).

Zhang et al., "A robust high-throughput sandwich cell-based drug screening platform," Biomaterials, 32(4):1229-124 (Feb. 1, 2011).

International Preliminary Report on Patentability for PCT/US2014/017785, dated Sep. 3, 2015, 8 pages.

International Preliminary Report on Patentability for PCT/US2014/017803, dated Sep. 3, 2015, 8 pages.

International Preliminary Report on Patentability in International Application No. PCT/US2013/066410, dated May 7, 2015, 8 pages.

International Search Report and Written Opinion for PCT/US2014/017785, dated May 20, 2014, 11 pages.

International Search Report and Written Opinion for PCT/US2014/017803, dated May 20, 2014, 11 pages.

International Search Report and Written Opinion in International Application No. PCT/US2015/034494, dated Nov. 30, 2015, 24 pages.

Invitation to Pay for PCT/US2015/034494, dated Aug. 12, 2015, 6 pages.

Notification of Transmittal of the International Search Report and the Written Opinion issued in PCT/US2013/066410 dated Jan. 31, 2014 (12 pages).

U.S. Appl. No. 14/061,657, filed Oct. 23, 2013, Yang et al.

U.S. Appl. No. 14/769,772, filed Aug. 21, 2015, Yang et al.

U.S. Appl. No. 62/009,058, filed Jun. 6, 2014, Villiger-Oberbek et al.

U.S. Appl. No. 62/095,734, filed Dec. 22, 2014, Bae et al.

U.S. Appl. No. 14/732,325, filed Jun. 5, 2015, Viliger-Oberbek et al.

Chinese Office Action in Application No. 2013-80067513.8, dated Apr. 13, 2016, 23 pages.

Clincke et al., "Very high density of CHO cells in perfusion by ATF or TFF in WAVE bioreactor. Part I. Effect of the cell density on the process", Biotechnol. Prog 29(3):754-767, May 2013.

Communication in European Office Action in European Application No. 13786587.9, dated Sep. 27, 2016, 10 pages.

Communication in European Office Action in European Application No. 13786587.9, dated Mar. 15, 2016, 5 pages.

Communication in European Office Action in European Application No. 14709829.7, dated Jun. 27, 2016, 5 pages.

Gargi, et al., "Development of a new bioprocess scheme using frozen seed train intermediates to initiate CHO cell culture manufacturing campaigns," Biotech. Bioeng. 110(5), pp. 1376-1385, May 4, 2013.

Gebauer and Skerra, "Engineered protein scaffolds as next-generation antibody therapeutics," Curr Opin Chem Biol., 13(3):245-255, Epub Jun. 6, 2009.

International Search Report and Written Opinion in International Application No. PCT/US2015/067040, dated Sep. 5, 2016, 17 pages.

International Search Report and Written Opinion in International Application No. PCT/US2015/034709, dated Oct. 30, 2015, 13 pages.

International Preliminary Report on Patentability in International Application No. PCT/US2013/066410, dated Jan. 31, 2014, 10 pages.

Fernandes-Platzgummer et al., "Scale-Up of Mouse Embryonic Stem Cell Expansion in Stirred Bioreactors", American Institute Chemical Engineers 27(5): 1421-1432, Sep.-Oct. 2011, Epub Jul. 25, 2011.

Final Office Action issued in U.S. Appl. No. 14/061,657, dated Aug. 19, 2016, 14 pages.

Katakam et al., "Effect of Surfactants on the physical stability of recombinant human growth hormone", Journal of Pharmaceutical Association, vol. 84, No. 6, Jun. 1, 1995, pp. 713-716.

Pohlscheidt et al., "Optimizing capacity utilization by large scale 3 000 L perfusion in seed train bioreactors," Biotechnology Progress, vol. 29, No. 1, 2220229, Jan. 1, 2012.

Written Opinion in Singapore Patent Application No. 11201506339R, dated Jul. 21, 2016.

Written Opinion in Singapore Patent Application No. 11201506343Q, dated Jun. 27, 2016, 5 pages.

Written Opinion in Singapore Patent Application No. 11201503085V, dated Dec. 7, 2016, 9 pages.

Senger et al., "Effect of shear stress on intrinsic CHO culture state and glycosylation of recombinant tissue-type plasminogen activator protein," Biotechnology Progress, vol. 19, No. 4, pp. 1199-209; Jul.-Aug. 2003; Abstract only.

Shi et al., "Expansion of Mouse Sertoli Cells on Microcarriers," Cell Proliferation, Apr. 2010, vol. 43, No. 3, pp. 275-286.

Smelko et al., Performance of high intensity fed-batch mammalian cell cultures in disposable bioreactor systems, Biotechnology Progress, 27(5):1358-1364, Sep. 2011.

Soyer et al., "Introducing shear stress in the study of bacterial adhesion," J. Vis. Exp. (55), e3241; 2011.

Tao et al., "Development and implementation of a perfusion-based high cell density cell banking process", Biotechnology Progress, vol. 27, No. 3, pp. 824-829, 2011.

Tordahl et al., "Study of a perfusion process of Chinese hamster ovary cells by ATF filtration in bioreactor ovary cells by ATF filtration in bioreactor", Sep. 11, 2009.

Villiger-Oberbek, Development and application of a high-throughput platform for perfustion-based cell culture processes, Journal of Biotechnology, 212, (2015) pp. 21-29.

Wright et al., "A novel seed-train process: using high-density cell banking, a disposable bioreactor, and perfusion technologies," Bio Process Int. Mar. 10, 2015 Supplement.

(56) References Cited

OTHER PUBLICATIONS

Yang et al., "Perfusion seed cultures improve biopharmaceutical fed-batch production capacity and product quality," Biotech. Prog. 30(3): 616-625, May 1, 2014.
Chinese Office Action in Application No. 201380067513.8, dated Jun. 6, 2017, 15 pages.
Chinese Office Action in Application No. 201480022715.5, dated May 15, 2017, 78 pages.
Chinese Office Action in Application No. 201480022766.8, dated May 4, 2017, 14 pages.
Chinese Office Action in Application No. 201380067513.8, dated Dec. 29, 2016.
Communication in European Office Action in European Application No. 13786587.9, dated Feb. 21, 2017, 4 pages.
Final Office Action in U.S. Appl. No. 14/769,772, dated May 9, 2017, 23 pages.
Final Office Action in U.S. Appl. No. 14/733,630, dated May 11, 2017, 14 pages.
International Preliminary Report on Patentability in International Application No. PCT/US2015/034494, dated Dec. 6, 2016, 14 pages.
Non-final Office Action in U.S. Appl. No. 14/733,630, dated Nov. 15, 2016, 13 pages.
Non-final Office Action issued in U.S. Appl. No. 14/769,772 dated Dec. 6, 2016.
Singapore Written Opinion in Application No. 11201506339R, dated Jul. 13, 2017, 4 pages.
Australian Office Action in Application No. 201334602, dated May 23, 2017, 2 pages.
Chinese Office Action in Application No. 201480022715.5, dated May 5, 2017, (62 pages including English Translation).
Communication in European Office Action in European Application No. 14709829.7, dated Aug. 31, 2017, 5 pages.
Communication in European Office Action in European Application No. 15730933.7 dated Oct. 23, 2017, 2 pages.
Communication in European Office Action in European Application No. 13786587.9, dated Nov. 28, 2017, 6 pages.
Communication in European Office Action in European Application No. 14709106.0, dated Oct. 17, 2017, 5 pages.
Corning-24, Corning Costar Ultra-low attachment mutiwell plates, Sigma-Aldrich, Catalog Webpage, Retrieved Jan. 10, 2018, Retrieved from: URL< https://www.sigmaaldrich.com/catalog/product/sigma/cls3473?lang=en&region=US, 3 pages.
Costa et al, The impact of microcarrier culture optimization on the glycosylation profile of a monoclonal antibody, Springer Plus, vol. 2, No. 25, Jan. 28, 2013, pp. 1-0.
Jayapal et al., "Recombinant Protein Therapeutics from CHO cells—20 years and counting", Chemical Engineering Progress, vol. 103, issue 10, Oct. 2007, pp. 40-47.
Non-Final Office Action issued in U.S. Appl. No. 14/732,325, dated Sep. 20, 2017, 10 pages.
Non-final Office Action issued in U.S. Appl. No. 14/061,657 dated Nov. 24, 2017, 9 pages.
Yizheng et al., Oxygen transfer reaction characteristics, Chemical Industry Press, Bioreaction Engineering, dated Jul. 31, 2004, pp. 134-139.
Schirmer et al., "Primary clarification of very high density cell culture harvests by enhanced cell settling", BioProcress International Jan. 2010, pp. 32-39.
Written Opinion in Singapore Patent Application No. 11201506339R, dated Jul. 20, 2017, 5 pages.
Written Opinion in Singapore Patent Application No. 1120160167W, dated Oct. 17, 2017, 7 pages.
Chinese Office Action in Application No. 201480022715.5, dated Feb. 13, 2018, 53 pages.
Chinese Office Action in Application No. 201480022715.5, dated Jul. 5, 2017, 16 pages.
Communication in European Office Action in European Application No. 13786587.9, dated Feb. 20, 2017, 6 pages.
Final Office Action in U.S. Appl. No. 14/769,783, dated Feb. 22, 2018, 19 pages.
Non-Final Office Action issued in U.S. Appl. No. 14/769,783, dated Oct. 10, 2017, 23 pages.
Non-Final Office Action issued in U.S. Appl. No. 14/733,630, dated Feb. 21, 2018, 6 pages.
Written Opinion in Australian Patent Application No. 2013334602, dated May 23, 2017, 2 pages.
Written Opinion in Singapore Application No. 11201503085V, dated Nov. 21, 2016, 9 pages.
Written Opinion in Singapore Patent Application No. 11201506339R, dated Jul. 21, 2016, 5 pages.
Written Opinion in Singapore Patent Application No. 11201506339R, dated Jul. 13, 2017, 7 pages.
Written Opinion in Singapore Patent Application No. 1120160167W, dated Oct. 12, 2017, 7 pages.
Written Opinion in Singapore Patent Application No. 11201610216U, dated Oct. 11, 2017, 6 pages.
Australian Office Action in Application No. 2014218715, dated Mar. 15 2019, 6 pages.
Chinese Office Action in Application No. 201480022766.8, dated Jan. 9, 2019, 35 pages.
Chinese Office Action in Application No. 201480022766.8, dated Jan. 3, 2018.
Extended European Search Report in Application No. 18205923.8, dated Jan. 14, 2019, 9 pages.
Huang et al., "Maximizing productivity of CHO cell-based fed-batch culture using chemically defined media conditions and typical manufacturing equipment," American Institute of Chemical Engineers Biotechnol. Prog. 26:1400-1410, Sep. 2010.
Mexican Office Action in Application No. MX/a/2015/010941, dated Nov. 20, 2018, 6 pages.
Singapore Examination Report in Application No. 11201503085V, dated Dec. 12, 2018, 7 pages.

* cited by examiner

MICROCARRIER PERFUSION CULTURING METHODS AND USES THEREOF

CROSS-REFERENCE TO RELATED APPLICATIONS

This application is a 371 U.S. National Stage Application of PCT Application No. PCT/US2014/017785, filed Feb. 21, 2014, which claims priority to U.S. Provisional Patent Application Ser. No. 61/768,215, filed Feb. 22, 2013, the entire contents of which are herein incorporated by reference.

TECHNICAL FIELD

This invention relates to methods of molecular biology, cell culture process development, and the manufacture of recombinant proteins.

BACKGROUND

Mammalian cells containing a nucleic acid that encodes a recombinant protein are often used to produce therapeutically or commercially important proteins. Although several high throughput (HT) cell culture systems have been used within the biotechnology industry for fed-batch processes for years, no HT model for a perfusion-based cell culture using shake tubes and microcarriers is known to exist.

Previous methods of mammalian tissue culture using shake tubes for feed batch cultures or perfusion cultures can produce recombinant proteins at high cell density; however, previous methods of culturing cells using a shake tube and microcarriers have been unsuccessful because of the shear stress inflicted on the mammalian cells by the circulating microcarriers, which results in a decrease in cell growth. In addition, it is difficult to harvest a recombinantly produced protein from a shake tube culture containing microcarriers.

SUMMARY

The present invention is based, at least in part, on the discovery that culturing a mammalian cell in the specific manner described herein (including the use of a shake tube and a plurality of microcarriers) results in actively growing mammalian cell cultures that effectively replicate the recombinant protein production achieved in a larger scale continuous-perfusion bioreactor containing microcarriers. Thus, the present specification includes methods of culturing a mammalian cell that include: providing a shake tube containing a mammalian cell disposed in a first liquid culture medium, where the first liquid culture medium occupies, e.g., about 10% to about 30% of the volume of the shake tube, and contains a plurality of microcarriers at a concentration of about 1.0 g/L to about 15.0 g/L; incubating the shake tube for a period of time at about 32° C. to about 39° C. and with a rotary agitation of about 120 revolutions per minute (RPM) to about 240 RPM (e.g., about 120 RPM to about 160 RPM); and after about the first 48 to 96 hours of the period of time, continuously or periodically removing a first volume of the first liquid culture medium and adding to the first liquid culture medium a second volume of a second liquid culture medium, where the first and second volumes are about equal. Also provided are various methods that utilize these culturing methods.

Provided herein are methods of culturing a mammalian cell. These methods include providing a shake tube containing a mammalian cell disposed in a first liquid culture medium, where the first liquid culture medium occupies about 10% to about 30% of the volume of the shake tube and contains a plurality of microcarriers at a concentration of about 1.0 g/L to about 15.0 g/L; incubating the shake tube for a period of time at about 32° C. to about 39° C. and with a rotary agitation of about 120 revolutions per minute (RPM) to about 240 RPM; and after about the first 48 to 96 hours of the period of time, continuously or periodically removing a first volume of the first liquid culture medium and adding to the first liquid culture medium a second volume of a second liquid culture medium, where the first and second volumes are about equal. In some embodiments of these methods, the first volume of the first liquid culture medium is substantially free of the microcarriers. In some embodiments of these methods, at the beginning of the period of time, the first liquid culture medium contains $0.1 \times 10^6$ cells/mL to $0.5 \times 10^6$ cells/mL. In some embodiments of any of these methods, the mammalian cell is a Chinese hamster ovary (CHO) cell. In some embodiments of any of these methods, the CHO cell contains a nucleic acid encoding a recombinant protein. In some embodiments of any of these methods, the recombinant protein is an immunoglobulin, an enzyme, a growth factor, a protein fragment, or an engineered protein. In some embodiments of any of these methods, the removing of the first volume of the first liquid culture medium and the adding of the second volume of the second liquid culture medium is performed simultaneously. In some embodiments of any of these methods, the removing of the first volume of the first liquid culture medium and the adding of the second volume of the second liquid culture medium is performed continuously. In some embodiments of any of these methods, the removing of the first volume of the first liquid culture medium and the adding of the second volume of the second liquid culture medium is performed periodically. In some embodiments of any of these methods, the first volume of the first liquid culture medium removed and the second volume of the second liquid culture medium added are increased over time. In some embodiments of any of these methods, the first liquid culture medium is the same as the second liquid culture medium. In some embodiments of any of these methods, the first liquid culture medium is different from the second liquid culture medium. In some embodiments of any of these methods, the shake tube has a volume of between about 10 mL to about 100 mL. In some embodiments of any of these methods, the mammalian cell is suspended in about 2 mL to about 20 mL of the first liquid culture medium. In some embodiments of any of these methods, the first liquid culture medium and/or second liquid culture medium is selected from the group consisting of: a chemically-defined liquid culture medium, a serum-free liquid culture medium, a serum-containing liquid culture medium, an animal-derived component free liquid culture medium, and a protein-free medium. In some embodiments of any of these methods, after about the first 48 to 96 hours of the period of time, in each 24-hour period, the first volume of the first liquid culture medium removed and the second volume of the second liquid culture medium added is about 30% to about 95% of the volume of the first liquid culture medium. In some embodiments of any of these methods, the agitation is ceased for a period of time of at least 30 seconds prior to removing the first volume of the first liquid culture medium. In some embodiments of any of these methods, the plurality of microcarriers has a mean diameter of between about 200 μm to about 800 m. In some embodiments of any of these methods, the plurality of microcarriers contains one or more pores. In some embodiments of any of these methods, the one or more pores has a mean diameter of about 25 µm to about 35 µm. In some embodiments of any of these methods, the shake tube is incubated at a reactor angle of about 25 degrees to about 90 degrees from horizontal.

Also provided are methods of culturing a mammalian cell that include: (a) providing a shake tube containing a mammalian cell disposed in a first liquid culture medium that occupies about 10% to about 30% of the volume of the shake tube and contains a plurality of microcarriers in a concentration of about 1.0 g/L to about 15.0 g/L; (b) incubating the shake tube for a first time period at about 35° C. to about 39° C. with a rotary agitation of about 120 revolutions per minute (RPM) to about 240 RPM, and after about the first 48 to 96 hours of the first period of time, in each subsequent 24-hour period, (i) continuously or periodically removing a first volume of the first liquid culture medium that is substantially free of microcarriers from the shake tube, where the first volume is about 10% to about 95% of the volume of the first liquid culture medium; and (ii) adding to the shake tube a second volume of a second liquid culture medium, where the first and second volumes are about equal; (c) incubating the shake tube after the cell concentration reaches about target cell density for a second time period of about 2 days to about 7 days, at about 32° C. to about 39° C. with the rotary agitation, and in each 24-hour period, performing steps (b)(i) and (b)(ii), where the first and second liquid culture media used in step (b) are of a substantially different type from those used in step (c); and (d) incubating the shake tube for a third time period greater than 2 days, at about 35° C. to about 39° C. with the rotary agitation, and in each 24-hour period, performing steps (b)(i) and (b)(ii), where the first and second liquid culture media used in step (c) are of the same type as those used in step (d).

In some embodiments of any of these methods, at the beginning of the first period of time, the first liquid culture medium contains $0.1 \times 10^6$ cells/mL to $0.5 \times 10^6$ cells/mL. In some embodiments of any of these methods, the mammalian cell is a Chinese hamster ovary (CHO) cell. In some embodiments of any of these methods, the CHO cell contains a nucleic acid encoding a recombinant protein. In some embodiments of any of these methods, the recombinant protein is a secreted immunoglobulin, a secreted enzyme, a secreted growth factor, a secreted protein fragment, or a secreted engineered protein. In some embodiments of any of these methods, the removing of the first volume of the first liquid culture medium, and the adding of the second volume of the second liquid culture medium in one or more of the first time period, the second time period, and the third time period is performed simultaneously. In some embodiments of any of these methods, the removing of the first volume of the first liquid culture medium, and the adding of the second volume of the second liquid culture medium in one or more of the first time period, the second time period, and the third time period is performed continuously. In some embodiments of any of these methods, the removing of the first volume of the first liquid culture medium, and the adding of the second volume of the second liquid culture medium in one of more of the first time period, the second time period, and the third time period is performed periodically. In some embodiments of any of these methods, the shake tube has a volume of between about 10 mL to about 100 mL. In some embodiments of any of these methods, the volume of the first liquid culture medium is about 2 mL to about 20 mL. In some embodiments of any of these methods, the first liquid culture medium and second liquid culture medium used in the first time period is serum-containing liquid culture medium or an animal-derived component-containing liquid culture medium, and the first liquid culture medium and the second liquid culture medium used in the second time period and the third time period is a serum-free liquid culture medium, an animal-derived component-free liquid culture medium, or a protein-free medium. In some embodiments of any of these methods, the agitation is ceased for at least 30 seconds prior to removing the first volume of the first liquid culture medium from the shake tube during one or more of the first time period, the second time period, and the third time period. In some embodiments of any of these methods, the plurality of microcarriers has a mean diameter of between about 200 µm to about 800 µm. In some embodiments of any of these methods, the plurality of microcarriers contains one or more pores. In some embodiments of any of these methods, the one or more pores has a mean diameter of about 25 µm to about 35 µm. In some embodiments of any of these methods, the first volume of the first liquid culture medium removed during the third period of time contains a substantial number of microcarriers. In some embodiments of any of these methods, the first volume of the first liquid culture medium removed during the third period of time is substantially free of microcarriers. In some embodiments of any of these methods, the first volume of the first liquid culture medium removed and the second volume of the second liquid culture medium added in one or more of the first time period, the second time period, and the third time period is about 70% of the volume of the first liquid culture medium. In some embodiments of any of these methods, the shake tube is incubated in one or more of (b), (c), and (d) at a reactor angle of about 25 degrees to about 90 degrees from horizontal.

Also provided are methods of producing a recombinant protein. These methods include: providing a shake tube containing a mammalian cell containing a nucleic acid encoding a recombinant protein disposed in a first liquid culture medium, where the first liquid culture medium occupies about 10% to about 30% of the volume of the shake tube and contains a plurality of microcarriers at a concentration of about 1.0 g/L to about 15.0 g/L; incubating the shake tube for a period of time at about 32° C. to about 39° C. and with a rotary agitation of about 120 revolutions per minute (RPM) to about 240 RPM; and after about the first 48 to 96 hours of the period of time, continuously or periodically removing a first volume of the first liquid culture medium and adding to the first liquid culture medium a second volume of a second liquid culture medium, where the first and second volumes are about equal; and recovering the recombinant protein from the mammalian cell or from the first and/or second liquid culture medium. In some embodiments of any of these methods, the recombinant protein is recovered from the mammalian cell. In some embodiments of any of these methods, the recombinant protein is recovered from the first and/or second liquid culture medium. In some embodiments of any of these methods, the first volume of the first liquid culture medium removed is substantially free of microcarriers. In some embodiments of any of these methods, at the beginning of the period of time, the first liquid culture medium contains $0.1 \times 10^6$ cells/mL to $0.5 \times 10^6$ cells/mL. In some embodiments of any of these methods, the mammalian cell is a Chinese hamster ovary (CHO) cell. In some embodiments of any of these methods, the recombinant protein is an immunoglobulin, an enzyme, a growth factor, a protein fragment, or an engineered protein. In some embodiments of any of these methods, the recombinant protein is secreted into the first and/or second liquid culture medium. In some embodiments of any of these methods, the removing of the first volume of the first liquid culture medium and the adding of the second volume of the second liquid culture medium is performed simultaneously. In some embodiments of any of these methods, the removing of the first volume of the first liquid culture medium and the adding of the second volume of the second liquid culture medium is performed continuously. In some embodiments of any of these methods, the removing of the first volume of the first liquid culture medium and the adding of the second volume of the second liquid culture medium is performed periodically. In some embodiments of any of these methods, the first volume of the first liquid culture medium removed and the second volume of the second liquid culture medium added are increased over time. In some embodiments of any of these methods, the first liquid culture medium is the same as the second liquid culture medium. In some embodiments of any of these methods, the first liquid culture medium is different from the second liquid culture medium. In some embodiments of any of these methods, the shake tube has a volume of between about 10 mL to about 100 mL. In some embodiments of any of these methods, the mammalian cell is suspended in about 2 mL to about 20 mL of the first liquid culture medium. In some embodiments of any of these methods, the first liquid culture medium and/or second liquid culture medium is selected from the group of: a chemically-defined liquid culture medium, a serum-free liquid culture medium, a serum-containing liquid culture medium, an animal-derived component-free liquid culture medium, and a protein-free medium. In some embodiments of any of these methods, after about the first 48 to 96 hours of the period of time, in each 24-hour period, the first volume of the first liquid culture medium removed and the second volume of the second liquid culture medium added is about 30% to about 95% of the volume of the first liquid culture medium. In some embodiments of any of these methods, the agitation is ceased for a period of time of at least 30 seconds prior to removing the first volume of the first liquid culture medium. In some embodiments of any of these methods, the plurality of microcarriers has a mean diameter of between about 200 µm to about 800 µm. In some embodiments of any of these methods, the plurality of microcarriers contains one or more pores. In some embodiments of any of these methods, the one or more pores has a mean diameter of about 25 µm to about 35 µm. In some embodiments of any of these methods, the shake tube is incubated at a reactor angle of about 25 degrees to about 90 degrees from horizontal.

Also provided are methods of producing a recombinant protein that include: (a) providing a shake tube containing a mammalian cell containing a nucleic acid encoding a recombinant protein disposed in a first liquid culture medium, where the first liquid culture medium occupies about 10% to about 30% of the volume of the shake tube and contains a plurality of microcarriers in a concentration of about 1.0 g/L to about 15.0 g/L; (b) incubating the shake tube for a first time period at about 35° C. to about 39° C. with a rotary agitation of about 120 revolutions per minute (RPM) to about 240 RPM, and after about the first 48 hours to 96 hours of the first period of time, in each subsequent 24-hour period, (i) continuously or periodically removing a first volume of the first liquid culture medium that is substantially free of microcarriers from the shake tube, where the first volume is about 10% to about 95% of the volume of the first liquid culture medium; and (ii) adding to the shake tube a second volume of a second liquid culture medium, where the first and second volumes are about equal; (c) incubating the shake tube after the cell concentration reaches about target cell density for a second time period of about 2 days to about 7 days, at about 32° C. to about 39° C. with the rotary agitation, and in each 24-hour period, performing steps (b)(i) and (b)(ii), where the first and second liquid culture media used in step (b) are of a substantially different type from those used in step (c); (d) incubating the shake tube for a third time period greater than 2 days, at about 35° C. to about 39° C. with the rotary agitation, and in each 24-hour period, performing steps (b)(i) and (b)(ii), where the first and second liquid culture media used in step (c) are of the same type as those used in step (d); and (e) recovering the recombinant protein from the mammalian cell or the first and/or second liquid culture medium used during the first, second, and/or third period of time. In some embodiments of any of these methods, the recombinant protein is recovered from the mammalian cell. In some embodiments of any of these methods, the recombinant protein is recovered from the first and/or second liquid culture medium used during one or more of the first, second, and third period of time. In some embodiments of any of these methods, at the beginning of the first period of time, the first liquid culture medium contains $0.1 \times 10^6$ cells/mL to $0.5 \times 10^6$ cells/mL. In some embodiments of any of these methods, the mammalian cell is a Chinese hamster ovary (CHO) cell. In some embodiments of any of these methods, the recombinant protein is an immunoglobulin, an enzyme, a growth factor, a protein fragment, or an engineered protein. In some embodiments of any of these methods, the recombinant protein is secreted into the first and/or second liquid culture medium used during one or more of the first period of time, the second period of time, and the third period of time. In some embodiments of any of these methods, the removing of the first volume of the first liquid culture medium and the adding of the second volume of the second liquid culture medium in one or more of the first time period, the second time period, and the third time period is performed simultaneously. In some embodiments of any of these methods, the removing of the first volume of the first liquid culture medium and the adding of the second volume of the second liquid culture medium in one or more of the first time period, the second time period, and the third time period is performed continuously. In some embodiments of any of these methods, the removing of the first volume of the first liquid culture medium and the adding of the second volume of the second liquid culture medium in one or more of the first time period, the second time period, and the third time period is performed periodically. In some embodiments of any of these methods, the shake tube has a volume of between about 10 mL to about 100 mL. In some embodiments of any of these methods, the volume of the first liquid culture medium is about 2 mL to about 20 mL. In some embodiments of any of these methods, the first liquid culture medium and second liquid culture medium used in the first time period is serum-containing liquid culture medium or an animal-derived component-containing liquid culture medium, and the first liquid culture medium and second liquid culture medium used in the second time period and the third time period is a serum-free liquid culture medium, an animal-derived component free liquid culture medium, or a protein-free medium. In some embodiments of any of these methods, the agitation is ceased for at least 30 seconds prior to removing the first volume of the first liquid culture medium, from the shake tube during one or more of the first time period, the second time period, and the third time period. In some embodiments of any of these methods, the plurality of microcarriers has a mean diameter of between about 200 µm to about 800 µm. In some embodiments of any of these methods, the plurality of microcarrier contains one or more pores. In some embodiments of any of these methods, the one or more pores has a mean diameter of about 25 μm to about 35 μm. In some embodiments of any of these methods, the first volume of the liquid culture medium removed during the third period of time contains a substantial number of microcarriers. In some embodiments of any of these methods, the first volume of the liquid culture medium removed during the third period of time is substantially free of microcarriers. In some embodiments of any of these methods, the first volume of the first liquid culture medium removed and the second volume of the second liquid culture medium added in one or more of the first time period, the second time period, and the third time period is about 70% of the volume of the first liquid culture medium. In some embodiments of any of these methods, the shake tube is incubated in one or more of (b), (c), and (d) at a reactor angle of about 25 degrees to about 90 degrees from horizontal.

Also provided are methods for testing a manufacturing process for making a recombinant protein. These methods include: providing a shake tube containing a mammalian cell containing a nucleic acid encoding a recombinant protein disposed in a first liquid culture medium, where the first liquid culture medium occupies about 10% to about 30% of the volume of the shake tube and contains a plurality of microcarriers at a concentration of about 1.0 g/L to about 15.0 g/L; incubating the shake tube for a period of time at about 32° C. to about 39° C. and with a rotary agitation of about 120 revolutions per minute (RPM) to about 240 RPM; after about the first 48 to 96 hours of the period of time, continuously or periodically removing a first volume of the first liquid culture medium and adding to the first liquid culture medium a second volume of a second liquid culture medium, where the first and second volumes are about equal; detecting the recombinant protein in the cell or in the first and/or second culture medium; and comparing the amount of recombinant protein present in the cell or in the first and/or second culture medium to a reference level of recombinant protein. In some embodiments of any of these methods, the first volume of the first liquid culture medium is substantially free of mammalian cells. In some embodiments of any of these methods, the reference level of recombinant protein is a level of recombinant protein produced using a different culturing method. In some embodiments of any of these methods, the different culturing method utilizes a different first or second liquid culture medium, a different mammalian cell, a different temperature, a different level of agitation, a different shake tube, or a different microcarrier. In some embodiments of any of these methods, the different culturing method utilizes a different raw material, anti-clumping agent, or chemically-defined liquid culture medium. In some embodiments of any of these methods, the method is used to perform high throughput cell culture experiments to perform a design-of-experiment (DOE) or a quality-by-design (QBD) study. In some embodiments of any of these methods, the shake tube is has a volume of between about 10 mL to about 100 mL. In some embodiments of these methods, the mammalian cell is suspended in about 2 mL to about 20 mL of the first liquid culture medium. In some embodiments of any of these methods, the mammalian cell is a Chinese hamster ovary (CHO) cell. In some embodiments of any of these methods, the recombinant protein is a secreted immunoglobulin, a secreted enzyme, a secreted growth factor, a secreted protein fragment, or a secreted engineered protein, and where the recombinant protein is recovered from the first or second culture medium. In some embodiments of any of these methods, the recombinant protein is recovered from the mammalian cell. In some embodiments of any of these methods, the recombinant protein is an immunoglobulin, an enzyme, a growth factor, a protein fragment, or an engineered protein. In some embodiments of any of these methods, the removing of the first volume of the first liquid culture medium and the adding of the second volume of the second liquid culture medium is performed simultaneously. In some embodiments of any of these methods, the removing of the first volume of the first liquid culture medium and the adding of the second volume of the second liquid culture medium is performed continuously. In some embodiments of any of these methods, the removing of the first volume of the first liquid culture medium and the adding of the second volume of the second liquid culture medium is performed periodically. In some embodiments of any of these methods, the first volume of the first liquid culture medium removed and the second volume of the second liquid culture medium added are increased over time. In some embodiments of any of these methods, the first liquid culture medium and/or second liquid culture medium is selected from the group consisting of: a chemically-defined liquid culture medium, a serum-free liquid culture medium, a serum-containing liquid culture medium, an animal-derived component free liquid culture medium, and a protein-free medium. In some embodiments of any of these methods, the shake tube incubated at a reactor angle of about 25 degrees to about 90 degrees from horizontal.

Also provided are methods of testing the efficacy of a first or second liquid culture medium, a raw ingredient or supplement present in a first or second liquid culture medium, or a source of a mammalian cell for use in a method of producing a recombinant protein. These methods include: providing a shake tube containing a mammalian cell disposed in a first liquid culture medium, where the first liquid culture medium occupies about 10% to about 30% of the volume of the shake tube and contains a plurality of microcarriers at a concentration of about 1.0 g/L to about 15.0 g/L; incubating the shake tube for a period of time at about 32° C. to about 39° C. and with a rotary agitation of about 120 revolutions per minute (RPM) to about 240 RPM; and after about the first 48 to 96 hours of the period of time, continuously or periodically removing a first volume of the first liquid culture medium and adding to the first liquid culture medium a second volume of a second liquid culture medium, where the first and second volumes are about equal; detecting the recombinant protein in the cell or in the first and/or second culture medium; comparing the amount of recombinant protein present in the cell or in the first and/or second culture medium to a reference level of recombinant protein produced by a different method that uses one or more of a different first or second liquid culture medium, a different raw ingredient or supplement present in the first or second liquid culture medium, or a different source of a mammalian cell; and identifying the first or second liquid culture medium, the raw ingredient or supplement present in the first or second liquid culture medium, or the source of the mammalian cell that is associated with an increased amount of recombinant protein as compared to the reference level as being efficacious for use in a method of producing a recombinant protein. In some embodiments of any of these methods, the shake tube is incubated at a reactor angle of about 25 degrees to about 90 degrees from horizontal.

Also provided are methods of optimizing a manufacturing process of producing a recombinant protein. These methods include: providing a shake tube containing a mammalian cell disposed in a first liquid culture medium, where the first liquid culture medium occupies about 10% to about 30% of the volume of the shake tube and contains a plurality of microcarriers at a concentration of about 1.0 g/L to about 15.0 g/L; incubating the shake tube for a period of time at about 32° C. to about 39° C. and with a rotary agitation of about 120 revolutions per minute (RPM) to about 240 RPM; and after about the first 48 to 96 hours of the period of time, continuously or periodically removing a first volume of the first liquid culture medium and adding to the first liquid culture medium a second volume of a second liquid culture medium, where the first and second volumes are about equal; detecting the recombinant protein in the cell or in the first and/or second culture medium; comparing the amount of recombinant protein present in the cell or in the first and/or second culture medium to a reference level of recombinant protein produced by a different method; and identifying and removing or altering in a manufacturing process any culture components or parameters that are associated with a decrease in the amount of recombinant protein produced as compared to the reference level, or identifying and adding to a manufacturing process any culture components or parameters that are associated with an increase in the amount of recombinant protein produced as compared to the reference level. In some embodiments of any of these methods, the shake tube is incubated at a reactor angle of about 25 degrees to about 90 degrees from horizontal.

Also provided are methods of testing for the presence of a contaminant in a first or second liquid culture medium, a raw material used to generate a first or second liquid culture medium, or a source of a mammalian cell. These methods include: providing a shake tube containing a mammalian cell disposed in a first liquid culture medium, where the first liquid culture medium occupies about 10% to about 30% of the volume of the shake tube and contains a plurality of microcarriers at a concentration of about 1.0 g/L to about 15.0 g/L; incubating the shake tube for a period of time at about 32° C. to about 39° C. and with a rotary agitation of about 120 revolutions per minute (RPM) to about 240 RPM; and after about the first 48 to 96 hours of the period of time, continuously or periodically removing a first volume of the first liquid culture medium and adding to the first liquid culture medium a second volume of a second liquid culture medium, where the first and second volumes are about equal; detecting the recombinant protein in the cell or in the first and/or second culture medium; comparing the amount of recombinant protein present in the cell or in the first and/or second culture medium to a reference level of recombinant protein produced by a different method that uses one or more of a different first or second liquid culture medium, a different raw material to generate the first or second liquid culture medium, or a different source of the mammalian cell; and identifying the first or second liquid culture medium, the raw material used to generate the first or second liquid culture medium, or the source of a mammalian cell as containing a contaminant when the level of recombinant protein produced is less than the reference level. In some embodiments of any of these methods, the contaminant is a biological contaminant. In some embodiments of any of these methods, the biological contaminant is selected from the group of: mycobacterium, a fungus, a bacterium, a virus, and an undesired mammalian cell. In some embodiments of any of these methods, the shake tube is incubated at a reactor angle of about 25 degrees to about 90 degrees from horizontal.

As used herein, the word "a" or "plurality" before a noun represents one or more of the particular noun. For example, the phrase "a mammalian cell" represents "one or more mammalian cells," and the phrase "plurality of microcarriers" means "one or more microcarriers."

The term "mammalian cell" means any cell from or derived from any mammal (e.g., a human, a hamster, a mouse, a green monkey, a rat, a pig, a cow, or a rabbit). In some embodiments, the mammalian cell can be, e.g., an immortalized cell, a differentiated cell, or an undifferentiated cell.

The term "target cell density" means a specific concentration of cells per volume of culture medium for producing a recombinant protein in culture. Target cell density can vary depending upon the specific mammalian cell cultured. For example, the target cell density can be about $1.0 \times 10^6$ cells/mL to about $50 \times 10^6$ cells/mL (e.g., between about $1.0 \times 10^6$ cells/mL to about $3.0 \times 10^6$ cells/mL, between about $1.0 \times 10^6$ cells/mL to about $2.0 \times 10^6$ cells/mL, or between about $2.0 \times 10^6$ cells/mL to about $3.0 \times 10^6$ cells/mL).

The term "substantially free" means a composition (e.g., a liquid culture medium) that is at least or about 90% free (e.g., at least or about 95%, 96%, 97%, 98%, or at least or about 99% free, or about 100% free) of a specific substance (e.g., a mammalian cell or microcarriers).

The term "culturing" or "cell culturing" means the maintenance or growth of a mammalian cell in a liquid culture medium under a controlled set of physical conditions.

The term "shake tube" is meant a vessel (e.g., a sterile vessel) that can retain liquid culture medium that has at least one gas permeable surface (e.g., an end that has at a gas-permeable element, e.g., a membrane, which may also act as a sterile barrier) and/or at least one vent cap, and is capable of retaining liquid culture medium within the vessel upon agitation (e.g., rotary agitation), and at least a portion of its shape is approximately cylindrical. For example, a shake tube can be an Eppendorf™ tube (e.g., a 50-mL or 15-mL Eppendorf™ tube), or any art-recognized equivalent or modified version thereof.

The term "liquid culture medium" means a fluid that contains sufficient nutrients to allow a mammalian cell to grow in the medium in vitro. For example, a liquid culture medium can contain one or more of: amino acids (e.g., 20 amino acids), a purine (e.g., hypoxanthine), a pyrimidine (e.g., thymidine), choline, inositol, thiamine, folic acid, biotin, calcium, niacinamide, pyridoxine, riboflavin, thymidine, cyanocobalamin, pyruvate, lipoic acid, magnesium, glucose, sodium, potassium, iron, copper, zinc, selenium, and other necessary trace metals, and sodium bicarbonate. A liquid culture medium may contain serum from a mammal. In some instances, a liquid culture medium does not contain serum or another extract from a mammal (a defined liquid culture medium). A liquid culture medium may contain trace metals, a mammalian growth hormone, and/or a mammalian growth factor. Non-limiting examples of liquid culture medium are described herein and additional examples are known in the art and are commercially available.

The phrase "substantially different type of liquid culture medium" means a liquid culture medium that contains a substantially different nutrient profile from another liquid culture medium. For example, a liquid culture medium that contains one or more of a mammalian serum, mammalian protein, or a mammalian protein fraction or extract (e.g., a serum-containing liquid culture medium) is a substantially different type of liquid culture medium than one that does not contain any of a mammalian serum, mammalian protein, or a mammalian protein fraction or extract (e.g., an animal-derived component free liquid culture medium, a serum-free liquid culture medium, a chemically-defined liquid culture medium, and a protein-free liquid culture medium).

The phrase "substantially the same type of liquid culture medium" means a liquid culture medium that contains about the same nutrient profile as compared to another liquid culture medium. For example, if liquid culture medium A and liquid culture medium B both contain one or more of a mammalian serum, mammalian protein, and a mammalian protein fraction or extract (e.g., a serum-containing liquid culture medium), there are substantially the same. In another example, if liquid culture medium A and liquid culture medium B both do not contain any of a mammalian serum, mammalian protein, and a mammalian protein fraction or extract (e.g., an animal-derived component free liquid culture medium, a serum-free liquid culture medium, a chemically-defined liquid culture medium, and a protein-free liquid culture medium), they are substantially the same.

The term "microcarrier" means a particle (e.g., an organic polymer) that has a size of between 20 µm to about 1000 µm that contains a surface that is permissive or promotes attachment of a mammalian cell (e.g., any of the mammalian cells described herein or known in the art). A microcarrier can contain one or more pores (e.g., pores with an average diameter of about 10 µm to about 100 µm). Non-limiting examples of microcarriers are described herein. Additional examples of microcarriers are known in the art. A microcarrier can contain, e.g., a polymer (e.g., cellulose, polyethylene glycol, or poly-(lactic-co-glycolic acid)).

The term "animal-derived component free liquid culture medium" means a liquid culture medium that does not contain any components (e.g., proteins or serum) derived from an animal.

The term "serum-free liquid culture medium" means a liquid culture medium that does not contain animal serum.

The term "serum-containing liquid culture medium" means a liquid culture medium that contains animal serum.

The term "chemically-defined liquid culture medium" means a liquid culture medium in which substantially all of the chemical components are known. For example, a chemically-defined liquid culture medium does not contain fetal bovine serum, bovine serum albumin, or human serum albumin, as these preparations typically contain a complex mix of albumins and lipids.

The term "protein-free liquid culture medium" means a liquid culture medium that does not contain any protein (e.g., any detectable protein).

"Rotary agitation" is a term well-known in the art and refers to the movement of a shake tube in a generally circular fashion, e.g., clock-wise or counter-clockwise, in order to, e.g., increase the dissolved $O_2$ concentration in a liquid culture medium contained therein. Agitation can be performed using any art-known method, e.g., an instrument that moves the shake tube in a circular or ellipsoidal motion, such as a rotary shaker. Exemplary devices that can be used to perform rotary agitation are described herein. Additional examples of such devices are also known in the art and are commercially available.

The term "immunoglobulin" means a polypeptide containing an amino acid sequence of at least 15 amino acids (e.g., at least 20, 30, 40, 50, 60, 70, 80, 90, or 100 amino acids) of an immunoglobulin protein (e.g., a variable domain sequence, a framework sequence, or a constant domain sequence). The immunoglobulin may, for example, include at least 15 amino acids of a light chain immunoglobulin and/or at least 15 amino acids of a heavy chain immunoglobulin. The immunoglobulin may be an isolated antibody (e.g., an IgG, IgE, IgD, IgA, or IgM). The immunoglobulin may be a subclass of IgG (e.g., IgG1, IgG2, IgG3, or IgG4). The immunoglobulin may be an antibody fragment, e.g., a Fab fragment, a $F(ab')_2$ fragment, or an a scFv fragment. The immunoglobulin may also be a bi-specific antibody or a tri-specific antibody, or a dimer, trimer, or multimer antibody, or a diabody, an Affibody®, or a Nanobody®. The immunoglobulin can also be an engineered protein containing at least one immunoglobulin domain (e.g., a fusion protein). Non-limiting examples of immunoglobulins are described herein and additional examples of immunoglobulins are known in the art.

The term "protein fragment" or "polypeptide fragment" means a portion of a polypeptide sequence that is at least or about 4 amino acids, e.g., at least or about 5 amino acids, at least or about 6 amino acids, at least or about 7 amino acids, at least or about 8 amino acids, at least or about 9 amino acids, at least or about 10 amino acids, at least or about 11 amino acids, at least or about 12 amino acids, at least or about 13 amino acids, at least or about 14 amino acids, at least or about 15 amino acids, at least or about 16 amino acids, at least or about 17 amino acids, at least or about 18 amino acids, at least or about 19 amino acids, or at least or about 20 amino acids in length, or more than 20 amino acids in length. A recombinant protein fragment can be produced using any of the methods described herein.

The term "engineered protein" means a polypeptide that is not naturally encoded by an endogenous nucleic acid present within an organism (e.g., a mammal). Examples of engineered proteins include enzymes (e.g., with one or more amino acid substitutions, deletions, insertions, or additions that result in an increase in stability and/or catalytic activity of the engineered enzyme), fusion proteins, antibodies (e.g., divalent antibodies, trivalent antibodies, or a diabody), and antigen-binding proteins that contain at least one recombinant scaffolding sequence.

The term "recover" or "recovering" in certain contexts means at least partially purifying or isolating (e.g., at least or about 5%, e.g., at least or about 10%, 15%, 20%, 25%, 30%, 40%, 45%, 50%, 55%, 60%, 65%, 70%, 75%, 80%, 85%, 90%, or at least or about 95% pure by weight) a recombinant protein from one or more other components present in the cell culture medium (e.g., mammalian cells or culture medium proteins) or one or more other components (e.g., DNA, RNA, or other proteins) present in a mammalian cell lysate. Non-limiting methods for recovering a protein from a liquid culture medium or from a mammalian cell lysate are described herein and others are known in the art.

The term "secreted protein" or "secreted recombinant protein" means a protein or a recombinant protein that originally contained at least one secretion signal sequence when it is translated within a mammalian cell, and through, at least in part, enzymatic cleavage of the secretion signal sequence in the mammalian cell, is released at least partially into the extracellular space (e.g., a liquid culture medium).

The phrase "gradient perfusion" is art-known and refers to the incremental change (e.g., increase or decrease) in the volume of culture medium removed and added to an initial culture volume over incremental periods (e.g., an about 24-hour period, a period of between about 1 minute and about 24-hours, or a period of greater than 24 hours) during the culturing period (e.g., the culture medium re-feed rate on a daily basis). The fraction of media removed and replaced each day can vary depending on the particular cells being cultured, the initial seeding density, and the cell density at a particular time.

The term "feed-batch culture" means the incremental or continuous addition of a second liquid culture medium to an initial cell culture without substantial or significant removal of the first liquid culture medium from the cell culture. In some instances, the second liquid culture medium is the same as the first liquid culture medium. In other instances, the second liquid culture medium is a concentrated form of the first liquid culture medium and/or is added as a dry powder.

The term "reactor angle" refers to the angle of deviation from the horizontal position that the shake tube containing a mammalian cell is placed during the culturing methods described herein. For example, when the shake tube containing a mammalian cell is a 50-mL conical tube and is standing vertical relative to the lab bench or ground, the reactor angle is 90°, and when the shake tube containing a mammalian cell is a 50-mL conical tube and is placed horizontal relative to the lab bench or ground, the reactor angle is 0°. In another example, when a shake tube containing a mammalian cell is a 50-mL conical tube and is placed equidistant between the vertical and horizontal positions (relative to the lab bench or ground), the reactor angle is 45°.

"Specific productivity rate" or "SPR" as used herein refers to the mass or enzymatic activity of a recombinant protein produced per mammalian cell per day. The SPR for a recombinant antibody is usually measured as mass/cell/day. The SPR for a recombinant enzyme is usually measured as units/cell/day or (units/mass)/cell/day.

"Volume productivity rate" or "VPR" as used herein refers to the mass or enzymatic activity of recombinant protein produced per volume of culture (e.g., per L of bioreactor, vessel, or tube volume) per day. The VPR for a recombinant antibody is usually measured as mass/L/day. The VPR for a recombinant enzyme is usually measured as units/L/day or mass/L/day.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1:
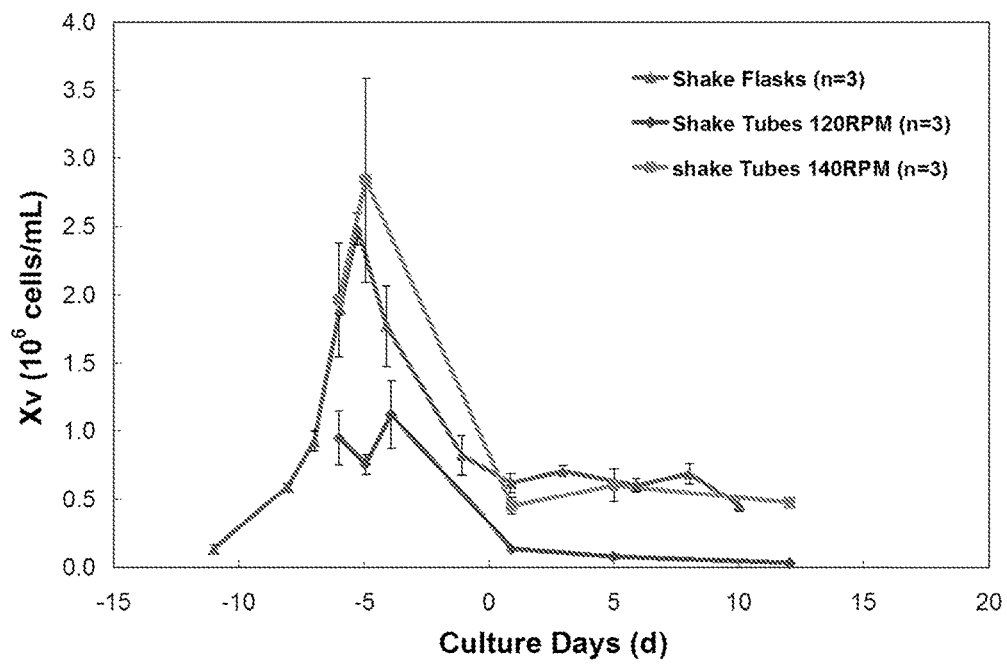
FIG. 1 is a graph of the viable cell concentration over time in shake tube cell culture process runs performed using an agitation frequency of 120 RPM (n=3) or 140 RPM (n=3), and in shake flask cell culture process runs (n=3). The mean of the data±standard deviation are shown.
Figure 2:
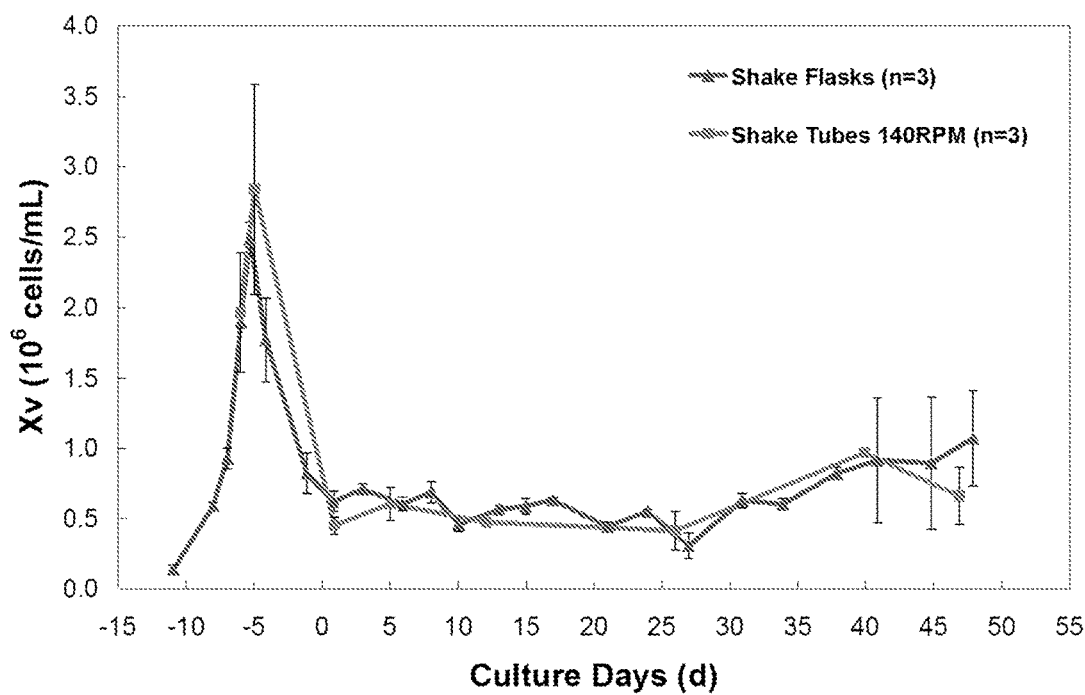
FIG. 2 is a graph of the viable cell concentration over time in shake tube cell culture process runs performed using an agitation frequency of 140 RPM (n=3) and in shake flask cell culture process runs (n=3). The mean of the data±standard deviation are shown.
Figure 3:
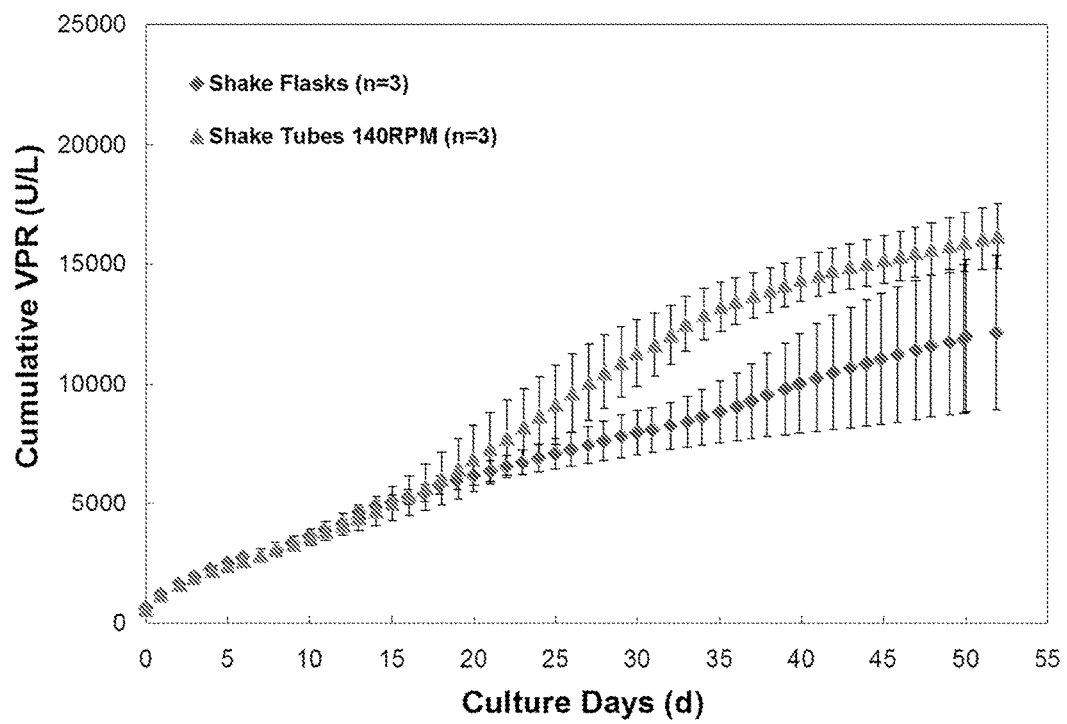
FIG. 3 is a graph of the cumulative volumetric productivity (units/L) over time in shake tube cell culture process runs performed using an agitation frequency of 140 RPM (n=3) and in shake flask cell culture process runs (n=3). The mean of the data±standard deviation are shown.

Provided herein are methods of culturing a mammalian cell in a shake tube using a plurality of microcarriers and batch re-feed perfusion. The culturing methods described herein can achieve high mammalian cell concentration levels, thereby improving the overall efficiency of a culturing process and providing high yields of desirable cellular products, such as recombinant proteins. For example, the methods can provide a viable mammalian cell concentration (e.g., in the first and/or second liquid culture medium, or the first and/or second liquid culture medium in one or more of the first, second, and third time periods) of greater than $2 \times 10^6$ cells per mL, greater than $3 \times 10^6$ cells/mL, greater than $4 \times 10^6$ cells/mL, greater than $5 \times 10^6$ cells/mL, greater than $6 \times 10^6$ cells/mL, greater than $7 \times 10^6$ cells/mL, greater than $8 \times 10^6$ cells/mL, greater than $9 \times 10^6$ cells/mL, greater than $10 \times 10^6$ cells/mL, greater than $12 \times 10^6$ cells/mL, greater than $14 \times 10^6$ cells/mL, greater than $16 \times 10^6$ cells/mL, greater than $18 \times 10^6$ cells/mL, greater than $20 \times 10^6$ cells/mL, greater than $25 \times 10^6$ cells/mL, greater than $30 \times 10^6$ cells/mL, greater than $35 \times 10^6$ cells/mL, greater than $40 \times 10^6$ cells/mL, greater than $45 \times 10^6$ cells/mL, or greater than $50 \times 10^6$ cells/mL. For example, the culturing method can result in a viable mammalian cell concentration of between $1 \times 10^6$ cells/mL and $3 \times 10^6$ cells/mL, between $3 \times 10^6$ cells/mL and $5 \times 10^6$ cells/mL, between $5 \times 10^6$ cells/mL and $7 \times 10^6$ cells/mL, between $7 \times 10^6$ cells/mL and $9 \times 10^6$ cells/mL, between $9 \times 10 \times 10^6$ cells/mL and $11 \times 10^6$ cells/mL, between $10 \times 10^6$ cells/mL and $12 \times 10^6$ cells/mL, between $11 \times 10^6$ cells/mL and $13 \times 10^6$ cells/mL, between $12 \times 10^6$ cells/mL and $14 \times 10^6$ cells/mL, between $14 \times 10^6$ cells/mL and $16 \times 10^6$ cells/mL, between $16 \times 10^6$ cells/mL and $18 \times 10^6$ cells/mL, between $18 \times 10^6$ cells/mL and $20 \times 10^6$ cells/mL, between $20 \times 10^6$ cells/mL and 25×10⁶ cells/mL, between 25×10⁶ cells/mL and 30×10⁶ cells/mL, between 30×10⁶ cells/mL and 35×10⁶ cells/mL, between 35×10⁶ cells/mL and 40×10⁶ cells/mL, between 40×10⁶ cells/mL and 45×10⁶ cells/mL, between 45×10⁶ cells/mL and 50×10⁶ cells/mL, or greater than 50×10⁶ cells/mL. In some instances, the methods described herein result in an increase in the biological activity of a recombinant protein (e.g., as compared to the biological activity of a recombinant protein produced by a different method).

A variety of different methods to determine the cell density or viable cell density can be used, and are well-known in the art. For example, a sample of the cell culture containing microcarriers can be treated to release the cells from the surface of the microcarriers, and the released cells can optionally be diluted in physiological buffer, and the cell suspension (e.g., diluted cell suspension) placed in a hemocytometer and counted using light microscopy. In another method, the viable cell density can be determined using a similar method, but including in the physiological buffer a dye that is selectively taken up by non-viable cells (e.g., trypan blue, such as Vi-CELL method from Beckman Coulter (see Beckman Coulter website)). In yet another example, the cell density or viable cell density can be determined using fluorescence-assisted flow cytometry (e.g., GUAVA from Merck Millipore (see Millipore website), and other cell counting methods.

In some instances, the culturing method results in a significantly improved specific productivity rate. For example, the specific productivity rate achieved by the methods provided herein can be at least 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 110-fold, 120-fold, 130-fold, 140-fold, 150-fold, 160-fold, 170-fold, 180-fold, 190-fold, or 200-fold greater than the specific productivity rate achieved using an art-known culturing method (e.g., a different shake tube culture method). The volume productivity rate achieved by the present methods can be at least 200 units/L/day, at least 300 units/L/day, at least 400 units/L/day, at least 500 units/L/day, at least 600 units/L/day, at least about 800 units/L/day, at least about 1,000 units/L/day, at least about 1,200 units/L/day, at least about 1,400 units/L/day, at least about 1,600 units/L/day, at least about 1,800 units/L/day, at least about 2,000 units/L/day, at least about 2,200 units/L/day, at least about 2,400 units/L/day, at least about 2,600 units/L/day, at least about 2,800 units/L/day, at least about 3,000 units/L/day, at least 4,000 units/L/day, at least 5,000 units/L/day, at least 6,000 units/L/day, at least 7,000 units/L/day, at least 8,000 units/L/day, at least 9,000 units/L/day, at least 10,000 units/L/day, higher than 1,000 units/L/day, or higher than 10,000 units/L/day (e.g., in the first and/or second liquid culture medium, or the first and/or second liquid culture medium used in one or more of the first, second, and third time period). In some embodiments, the productivity achieved by the present methods can be at least 0.1 g/L, at least 0.2 g/L, at least 0.5 g/L, at least 0.75 g/L, at least 1.0 g/L, at least 1.25 g/L, at least 1.5 g/L, at least 1.75 g/L, at least 2.0 g/L, at least 2.5 g/L, at least 3.0 g/L, at least 3.5 g/L, at least 4.0 g/L, at least 4.5 g/L, or at least 5.0 g/L (e.g., in the first and/or second liquid culture medium, or the first and/or second liquid culture medium used in the first, second, and third time period).

The biological activity of a recombinant protein can be assessed using a variety of methods known in the art, and will depend on the activity of the specific recombinant protein. For example, the biological activity of a recombinant protein that is an immunoglobulin (e.g., an antibody or an antibody fragment) can be determined by measuring the affinity of the antibody to bind to its specific epitope (e.g., using Biocore or competitive enzyme-linked immunosorbent assays). The recombinant protein may be an enzyme (e.g., a recombinant galactosidase, e.g., a recombinant human alpha-galactosidase) and the biological activity may be determined by measuring the enzyme's activity (e.g., determining the catalytic rate constant of the enzyme by measuring a decrease in the concentration of a detectable substrate or an increase in the concentration of a detectable product (e.g., using spectrophotometry or light emission). For example, the biological activity of a recombinant galactosidase can be detected by measuring a decrease in the level of globotriasylceramide (GL-3) or galabiosylceramide, or an increase in the level of ceramide dihexoside or galactose.

Methods of Culturing a Mammalian Cell

In a method that is exemplary of those described herein, a shake tube is provided. A first liquid culture medium is added to the shake tube such that the medium occupies, e.g., about 10% to about 30% (e.g., about 10% to about 20%, about 20% to about 30%, about 10% to about 12%, about 12% to about 14%, about 14% to about 16%, about 16% to about 18%, about 18% to about 20%, about 20% to about 22%, about 22% to about 24%, about 24% to about 26%, about 26% to about 28%, about 28% to about 30%, about 10% to about 15%, about 15% to about 20%, about 20% to about 25%, or about 25% to about 30%) of the volume of the shake tube. At least one mammalian cell and a plurality of microcarriers (a final concentration in the shake tube of about 1.0 g/L to about 15.0 g/L, e.g., a final concentration in the shake tube of between about 1.0 g/L to about 2.5 g/L, about 1.0 g/L to about 2.0 g/L, about 1.0 g/L to about 1.75 g/L, about 1.0 g/L to about 1.5 g/L, about 1.0 g/L to about 1.25 g/L, about 2.5 g/L to 5.0 g/L, about 5.0 g/L to about 7.5 g/L, about 7.5 g/L to about 10.0 g/L, about 10.0 g/L to about 12.5 g/L, about 12.5 g/L to about 15.0 g/L, about 1.0 g/L to about 5.0 g/L, about 5.0 g/L to about 10.0 g/L, about 10.0 g/L to about 15.0 g/L, about 2.5 g/L to about 3.5 g/L, about 3.0 g/L to about 4.0 g/L, about 4.0 g/L to about 5.0 g/L, about 5.0 g/L to about 6.0 g/L, about 6.0 g/L to about 7.0 g/L, about 7.0 g/L to about 8.0 g/L, about 8.0 g/L to about 9.0 g/L, about 9.0 g/L to about 10.0 g/L, about 10.0 g/L to about 11.0 g/L, about 11.0 g/L to about 12.0 g/L, about 12.0 g/L to about 13.0 g/L, about 13.0 g/L to about 14.0 g/L, or about 14.0 g/L to about 15.0 g/L) is added to the first liquid culture medium, i.e., either before the medium is added to the shake tube or afterward. As one skilled in the art can appreciate, the steps of the addition of the liquid culture medium, a mammalian cell, and the liquid culture medium to the shake tube can occur in any order. The shake tube is incubated for a period of time at about 32° C. to about 39° C. (e.g., 32° C. to 34° C., 32° C. to 37° C., 34° C. to 37° C., 37° C. to 39° C.) and agitated, e.g., on a rotary shaking device, at about 120 RPM to about 240 RPM (e.g., about 120 RPM to about 230 RPM, about 120 RPM to about 220 RPM, about 120 RPM to about 210 RPM, about 120 RPM to about 200 RPM, about 120 RPM to about 190 RPM, about 120 RPM to about 180 RPM, about 120 RPM to about 170 RPM, about 120 RPM to about 160 RPM, about 120 RPM to about 150 RPM, about 130 RPM to about 180 RPM, about 130 RPM to about 170 RPM, about 140 RPM to about 170 RPM, about 150 RPM to about 170 RPM, about 120 RPM to about 140 RPM, about 130 RPM to about 150 RPM, about 140 RPM to about 160 RPM, about 150 RPM to about 170 RPM, about 160 RPM to about 180 RPM, about 160 RPM to about 220 RPM, about 160 RPM to about 210 RPM, about 150 RPM to about 190 RPM, or about 180 RPM to about 210

RPM). The cells can be incubated, for example, in an incubator, such as a shake incubator with throw (orbit) diameter of 25 mm or from about 3 mm to about 50 mm, while changing the RPM accordingly. After the first 48 to 96 hours of the period of time of incubation, continuously or periodically over the period of time, a first volume of the first liquid culture medium (e.g., containing any mammalian cell concentration, e.g., a first volume of first liquid culture medium which is or is made substantially free of mammalian cells and/or microcarriers) is removed, and a second volume of a second liquid culture medium is added to the first liquid culture medium. Typically, the first and the second volumes are roughly equal, but can vary by a small amount, e.g., by up to about 10% when the first and second volumes are compared. In some embodiments, the second volume of the second liquid culture medium added is less (e.g., at most about 1%, 2%, 3%, 4%, 5%, 6%, 7%, 8%, 9%, or 10% less) or more (e.g., at most about 1%, 2%, 3%, 4%, 5%, 6%, 7%, 8%, 9%, or 10% more) than the first volume of the first liquid culture medium removed. As is known in the art, the term incubating can include short periods of time (e.g., between 10 seconds and about 10 minutes, between 10 seconds and about 20 minutes, between 10 seconds and about 30 minutes, between 10 seconds and about 40 minutes, between about 10 seconds and about 50 minutes, or between 10 seconds and about 1 hour) in which a shake tube containing the mammalian cell and liquid culture medium is removed from an incubator in order to remove the first volume of the first liquid culture medium and add the second volume of the second liquid culture medium. In some embodiments, an automatic sampler can be employed to remove the first volume of the first culture medium and add the second volume of the second liquid culture medium to the shake tube while the shake tube remains in the incubator.

In another exemplary method, a shake tube is first provided. A first liquid culture medium is added to the shake tube such that the medium occupies, e.g., about 10% to about 30% (e.g., about 10% to about 20%, about 20% to about 30%, about 10% to about 12%, about 12% to about 14%, about 14% to about 16%, about 16% to about 18%, about 18% to about 20%, about 20% to about 22%, about 22% to about 24%, about 24% to about 26%, about 26% to about 28%, about 28% to about 30%, about 10% to about 15%, about 15% to about 20%, about 20% to about 25%, or about 25% to about 30%) of the volume of the shake tube. At least one mammalian cell and a plurality of microcarriers (a final concentration in the shake tube of about 1.0 g/L to about 15.0 g/L, e.g., a final concentration in the shake tube of between about 1.0 g/L to about 2.5 g/L, about 1.0 g/L to about 2.0 g/L, about 1.0 g/L to about 1.75 g/L, about 1.0 g/L to about 1.5 g/L, about 1.0 g/L to about 1.25 g/L, about 2.5 g/L to 5.0 g/L, about 5.0 g/L to about 7.5 g/L, about 7.5 g/L to about 10.0 g/L, about 10.0 g/L to about 12.5 g/L, about 12.5 g/L to about 15.0 g/L, about 1.0 g/L to about 5.0 g/L, about 5.0 g/L to about 10.0 g/L, about 10.0 g/L to about 15.0 g/L, about 2.5 g/L to about 3.5 g/L, about 3.0 g/L to about 4.0 g/L, about 4.0 g/L to about 5.0 g/L, about 5.0 g/L to about 6.0 g/L, about 6.0 g/L to about 7.0 g/L, about 7.0 g/L to about 8.0 g/L, about 8.0 g/L to about 9.0 g/L, about 9.0 g/L to about 10.0 g/L, about 10.0 g/L to about 11.0 g/L, about 11.0 g/L to about 12.0 g/L, about 12.0 g/L to about 13.0 g/L, about 13.0 g/L to about 14.0 g/L, or about 14.0 g/L to about 15.0 g/L) is added to the first liquid culture medium, i.e., either before the medium is added to the shake tube or afterward. As noted above, the addition of the liquid culture medium, a mammalian cell, and the liquid culture medium to the shake tube can occur in any order. Then, in a first time period, the shake tube is incubated at about 35° C. to about 39° C. (e.g., 35° C. to 37° C., 36° C. to 39° C., or 37° C. to 39° C.) with a rotary agitation of about 120 RPM to about 240 RPM (e.g., about 120 RPM to about 230 RPM, about 120 RPM to about 220 RPM, about 120 RPM to about 210 RPM, about 120 RPM to about 200 RPM, about 120 RPM to about 190 RPM, about 120 RPM to about 180 RPM, about 120 RPM to about 170 RPM, about 120 RPM to about 160 RPM, about 120 RPM to about 150 RPM, about 130 RPM to about 180 RPM, about 130 RPM to about 170 RPM, about 140 RPM to about 170 RPM, about 150 RPM to about 170 RPM, about 120 RPM to about 140 RPM, about 130 RPM to about 150 RPM, about 140 RPM to about 160 RPM, about 150 RPM to about 170 RPM, about 160 RPM to about 180 RPM, about 160 RPM to about 220 RPM, about 160 RPM to about 210 RPM, about 150 RPM to about 190 RPM, or about 180 RPM to about 210 RPM). The cells can be incubated, for example, in an incubator, such as a shake incubator with throw (orbit) diameter from about 3 mm to about 50 mm. After about the first 48 to 96 hours of the first time period, in each subsequent 24-hour period, (i) continuously or periodically removing a first volume of the first liquid culture medium that is substantially free of microcarriers from the shake tube, wherein the first volume is about 10% to about 95% (e.g., about 10% to 20%, about 20% to about 30%, about 30% to about 40%, about 40% to about 50%, about 50% to about 60%, about 60% to about 70%, about 70% to about 80%, about 80% to about 95%, about 50% to about 95%, about 50% to about 90%, or about 60% to about 90%) of the volume of the first liquid culture medium; and (ii) adding to the shake tube a second volume of a second liquid culture medium, wherein the first and second volume are about equal. As noted above, the first and the second volumes are roughly equal, but can vary by a small amount, e.g., by up to about 10% when the first and second volumes are compared. Once the cell concentration reaches about target cell density (e.g., about $1.0 \times 10^6$ cells/mL, about $1.5 \times 10^6$ cells/mL, about $2.0 \times 10^6$ cells/mL, about $2.2 \times 10^6$ cells/mL, about $2.4 \times 10^6$ cells/mL, about $2.6 \times 10^6$ cells/mL, about $2.8 \times 10^6$ cells/mL, about $3.0 \times 10^6$ cells/mL, about $3.2 \times 10^6$ cells/mL, about $3.4 \times 10^6$ cells/mL, about $3.6 \times 10^6$ cells/mL, about $3.8 \times 10^6$ cells/mL, about $4.0 \times 10^6$ cells/mL, about $1.0 \times 10^6$ cells/mL to $4.0 \times 10^6$ cells/mL, about $2.0 \times 10^6$ cells/mL to about $4.0 \times 10^6$ cells/mL, about $2.0 \times 10^6$ cells/mL to about $4.0 \times 10^6$ cells/mL, about $4.0 \times 10^6$ cells/mL to about $6.0 \times 10^6$ cells/mL, about $6.0 \times 10^6$ cells/mL to about $8.0 \times 10^6$ cells/mL, about $8.0 \times 10^6$ cells/mL to about $10.0 \times 10^6$ cells/mL, about $10.0 \times 10^6$ cells/mL to about $15.0 \times 10^6$ cells/mL, about $15.0 \times 10^6$ to about $20.0 \times 10^6$ cells/mL, about $20.0 \times 10^6$ cells/mL to about $25.0 \times 10^6$ cells/mL, about $25.0 \times 10^6$ cells/mL to about $30.0 \times 10^6$ cells/mL, about $30.0 \times 10^6$ cells/mL to about $35.0 \times 10^6$ cells/mL, about $35.0 \times 10^6$ cells/mL to about $40.0 \times 10^6$ cells/mL, about $40.0 \times 10^6$ cells/mL to about $45.0 \times 10^6$ cells/mL, or about $45.0 \times 10^6$ cells/mL to about $50.0 \times 10^6$ cells/mL) the shake tube is incubated for a second time period of about 2 days to about 7 days (e.g., about 2 days to about 4 days, about 3 days to about 5 days, about 4 days to about 6 days, and about 5 days to about 7 days), at about 32° C. to about 39° C. (e.g., about 32° C. to about 35° C., about 32° C. to about 37° C., about 32° C. to about 38° C., about 34° C. to about 39° C., about 34° C. to about 37° C., about 35° C. to about 38° C., about 35° C. to about 39° C., about 36° C. to about 39° C., or about 37° C. to about 39° C.) with the rotary agitation, and in each 24-hour period, performing steps (i) and (ii) described above, where the first and second liquid culture media used in the first time period are of a substantially different type from those used in the second time period. Then, in a third period of time of greater than 2 days (e.g., 2, 3, 4, 5, 6, 7, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 days, greater than 100 days, 110 days, 120 days, 130 days, 140 days, 150 days, 160 days, 170 days, 180 days, 190 days, or 200 days, or at most 100 days, 125 days, 150 days, 175 days, 200 days, 225 days, 250 days, 275 days, or 300 days) incubating the shake tube at about 35° C. to about 39° C. (e.g., about 35° C. to about 37°, 36° C. to about 38° C., about 37° C. to about 39° C., or about 36° C. to about 39° C.) with the rotary agitation, and in each 24-hour period, performing steps (i) and (ii) listed above, where the first and second liquid culture media used in the second time period are of the same type as those used in the third time period.

Various non-limiting examples of each aspect of these culturing methods are described below. The exemplary aspects of the methods provided herein can be used in any combination without limitation.

Mammalian Cells

The methods provided herein can be used to culture a variety of different mammalian cells. In some examples of all the methods described herein, the mammalian is an adherent cell. Non-limiting examples of mammalian cells that can be cultured using any of the methods described herein include: Chinese hamster ovary (CHO) cells (e.g., CHO DG44 cells, CHO-K1s cells, Sp2.0, myeloma cells (e.g., NS/0), B-cells, hybridoma cells, T-cells, human embryonic kidney (HEK) cells (e.g, HEK 293E and HEK 293F), African green monkey kidney epithelial cells (Vero) cells, and Madin-Darby Canine (Cocker Spaniel) kidney epithelial cells (MDCK) cells. Additional mammalian cells that can be cultured using the methods described herein are known in the art.

The mammalian cell can contain a recombinant nucleic acid (e.g., a nucleic acid stably integrated in the mammalian cell's genome) that encodes a recombinant protein (e.g., a recombinant protein that is secreted by the mammalian cell). Non-limiting examples of recombinant nucleic acids that encode exemplary recombinant proteins are described below, as are recombinant proteins that are producible using the methods described herein. In some instances, the mammalian cell disposed in the shake tube for culturing is derived from a larger culture. For example, the mammalian cell in the shake tube can be derived from a large-scale bioreactor culture, i.e., a satellite culture can be prepared using any of the methods described herein.

Culture Media

Liquid culture media are known in the art. The first and/or second tissue culture medium (e.g., the first and second liquid culture medium used in the first time period or the second and third time periods) can be supplemented with a mammalian serum (e.g., fetal calf serum and bovine serum), and/or a growth hormone or growth factor (e.g., insulin, transferrin, and epidermal growth factor). Alternatively or in addition, the first and/or second liquid culture medium (e.g., the first and/or second liquid culture medium, e.g., the first and/or second liquid culture medium in the first time period or the second and third time periods) can be a chemically-defined liquid culture medium, an animal-derived component free liquid culture medium, a serum-free liquid culture medium, or a serum-containing liquid culture medium. Non-limiting examples of chemically-defined liquid culture media, animal-derived component free liquid culture media, serum-free liquid culture media, and serum-containing liquid culture media are commercially available.

A liquid culture medium typically contains an energy source (e.g., a carbohydrate, such as glucose), essential amino acids (e.g., the basic set of twenty amino acids plus cysteine), vitamins and/or other organic compounds required at low concentrations, free fatty acids, and/or trace elements. The first and/or second liquid culture medium (e.g., the first and/or second liquid culture medium used in the first time period or the second and third time periods) can, if desired, be supplemented with, e.g., a mammalian hormone or growth factor (e.g., insulin, transferrin, or epidermal growth factor), salts and buffers (e.g., calcium, magnesium, and phosphate salts), nucleosides and bases (e.g., adenosine, thymidine, and hypoxanthine), protein and tissue hydrolysates, and/or any combination of these or other additives.

Non-limiting examples of liquid culture media that are particularly useful in the presently described methods include, e.g., CD CHO, Opti CHO, and Forti CHO (all available from Life Technologies; Grand Island, N.Y.), Hycell CHO medium (Thermo Fisher Scientific, Inc.; Waltham, Mass.), Ex-cell CD CHO Fusion medium (Sigma-Aldrich Co.; St. Louis, Mo.), and PowerCHO medium (Lonza Group, Ltd.; Basel, Switzerland). Medium components that also may be useful in the present methods include, but are not limited to, chemically-defined (CD) hydrolysates, e.g., CD peptone, CD polypeptides (two or more amino acids), and CD growth factors. Additional examples of liquid tissue culture medium and medium components are known in the art.

Skilled practitioners will appreciate that the first liquid culture medium and the second liquid culture medium described herein can be the same type of media or different type of media. For example, in examples of the methods that include a first time period, a second time period, and a third time period, the first and second liquid culture medium used in the first time period are substantially different from the first and second liquid culture medium used in the second and third time period, and the first and second liquid culture medium used in the second and third time period are substantially the same. For example, the first and second liquid culture medium used in the first time period can be selected from the group consisting of a serum-containing liquid culture medium or a liquid culture medium that contains a mammalian protein or a mammalian protein fraction or extract, and the first and second liquid culture medium used in the second and third time periods can be selected from the group of: an animal-derived component free liquid culture medium, a serum-free liquid culture medium, a chemically-defined liquid culture medium, and a protein-free liquid culture medium.

Microcarriers

In the methods described herein, a plurality of microcarriers is added to the liquid culture medium (e.g., the first and/or second liquid culture medium). For example, the plurality of microcarriers can have an average diameter of between about 20 μm to about 1 mm (e.g., between about 20 μm and about 250 μm, between about 100 μm to about 250 μm, between about 150 μm to about 250 μm, between about 250 μm and 500 μm, between about 200 μm to about 300 μm, between about 750 μm and 1 mm, between about 200 μm to about 800 μm, between about 200 μm and about 500 μm, or between about 500 μm and about 800 μm), where the microcarriers have a surface that is permissive or promotes attachment of a mammalian cell (e.g., any of the mammalian cells described herein or known in the art). In some examples, a microcarrier can contain one or more pores (e.g., one or more pores with an average diameter of about 10 µm to about 100 µm (e.g., between about 10 µm and 20 µm, about 20 µm to about 30 µm, about 30 µm to about 40 µm, about 50 µm to about 60 µm, about 60 µm to about 70 µm, about 70 µm to about 80 µm, about 80 µm to about 90 µm, about 90 µm to about 100 µm, about 10 µm to about 45 µm, about 45 µm to about 80 µm, about 25 µM to about 35 µm, or about 30 µm)). In some embodiments, the surface of the plurality of microcarriers and/or the surface of the one or more pores in the plurality of microcarriers are coated with an agent that promotes the attachment of a mammalian cell to the microcarrier (e.g., attachment to the outer surface of the microcarriers and/or the surface of the pores in the microcarrier). Examples of such agents that can be used to promote the attachment of a mammalian cell include, but are not limited to, gelatin, collagen, poly-L-ornithine, polystyrene, and laminin.

In some examples, the microcarriers have an average effective cell binding surface area of between about 0.5 m$^2$/g dry and 2.0 m$^2$/g dry (e.g., between about 0.75 m$^2$/g dry and 1.25 m$^2$/dry, between about 1.0 m$^2$/g dry and about 1.5 m$^2$/dry, between about 1.25 m$^2$/dry and about 1.5 m$^2$/dry, between about 1.5 m$^2$/dry and about 2.0 m$^2$/dry, and about 1.1 m$^2$/dry). In some examples, the microcarriers have an average volume of about 10 mL/g dry to about 70 mL/g dry (e.g., about 10 mL/g dry to about 20 mL/g dry, about 20 mL/g dry to about 30 mL/g dry, about 30 mL/g dry to about 40 mL/g dry, about 40 mL/g dry to about 50 mL/g dry, about 50 mL/g dry to about 60 mL/g dry, about 60 mL/g dry to about 70 mL/g dry, about 10 mL/g dry to about 40 mL/g dry, about 30 mL/g dry to about 40 mL/g dry, about 40 mL/g dry to about 70 mL/g dry, or about 40 mL/g dry). In some embodiments, the average relative density of the microcarriers is between 0.8 g/mL to about 1.2 g/mL (e.g., about 0.8 g/mL to about 0.9 g/mL, about 0.9 g/mL to about 1.0 g/mL, about 1.0 g/mL to about 1.1 g/mL, about 1.0 g/mL, about 1.1 g/mL to about 1.2 g/mL, about 0.95 g/mL to about 1.05 g/mL, or about 1.03 g/mL).

In some embodiments, the microcarriers are approximately spherical or ellipsoidal in shape. In other examples, the microcarriers have an abraded or rough surface with small protuberances that increase the total outer surface area of the microcarrier. In some embodiments, the microcarriers have a network structure. In some examples, the microcarriers are hygroscopic. In some examples, the microcarriers contain cellulose.

In some embodiments, the microcarriers have an outer surface and/or the microcarrier pores have a surface that is positively charged (e.g., positively charged due to the presence of N,N-diethylaminoethyl groups). In some examples, the microcarriers have a network or net-like or web-like structure. The microcarriers can have an average charge density of about 0.5 meq/g to about 2.5 meq/g (e.g., about 0.5 meq/g to about 1.5 meq/g, about 0.75 meq/g to about 1.25 meq/g, about 1.1 meq/g, about 1.5 meq/g to about 2.5 meq/g, about 1.5 meq/g to about 2.0 meq/g, about 1.8 meq/g, about 0.5 meq/g to about 1.0 meq/g, or about 1.0 meq/g to about 1.5 meq/g).

In some instances, the microcarrier can contain a natural polymer and/or a synthetic polymer. Non-limiting examples of synthetic polymers include polyethylene glycol (PEG), polyethylene oxide, polyethyleneimine, diethyleneglycol, triethyleneglycol, polyalkalene glycol, polyalkaline oxide, polyvinyl alcohol, sodium polyphosphate, polyvinylpyrrolidone, polyvinylmethylether, polymethyloxazoline, polyethyloxazoline, polyhydroxypropyloxazoline, polyhydroxypropylmethacrylamide, polymethacrylamide, polydimethylacrylamide, polyhydroxypropylmethacrylate, polyhydroxyethylacrylate, hydroxymethylcellulose, hydroxyethylcellulose, polyglycerine, polyaspartamide, polyoxyethlene-polyoxypropylene copolymer (poloxamer), carboxylic acids (e.g., acrylic acid, methacrylic acid, itaconic acid, and maleic acid), polyoxyethylenes, polyethyleneoxide, unsaturated ethylenic monodicarboxylic acids, polylactic acid (PLA), polypropylene oxide, poly(lactide-co-glycolide) (PLGA), poly(epsilon-caprolactone), poly (ethylethylene), polybutadiene, polyglycolide, polymethylacrylate, polyvinylbutylether, polystyrene, polycyclopentadienylmethylnorbornene, polyethylenepropylene, polyethylethylene, polyisobutylene, polysiloxane, methyl acrylate, ethyl acrylate, propyl acrylate, n-butyl acrylate, isobutyl acrylate, 2-ethyl acrylate, t-butyl acrylate, methacrylates (e.g., ethyl methacrylate, n-butyl methacrylate, and isobutyl methacrylate), acrylonitriles, methacrylonitrile, vinyls (e.g., vinyl acetate, vinylversatate, vinylpropionate, vinylformamide, vinylacetamide, vinylpyridines, and vinylimidazole), aminoalkyls (e.g., aminoalkylacrylates, aminoalkylsmethacrylates, and aminoalkyl(meth) acrylamides), styrenes, polyalkalene glycol, polyalkaline oxide, and lactic acids. Non-limiting examples of natural polymers include cellulose, lecithin, and hyaluronic acid. A microcarrier can contain a mixture of different polymers (e.g., any combination of one or more polymers described herein or known in the art) in the same or different ratios. Any of the microcarriers described herein can contain a core containing one or more polymers (e.g., any of the polymers described herein or known in the art) and an outer layer that contains one or more different polymers (e.g., any of the polymers described herein or known in the art). A plurality of microcarriers can include a combination of two or more different types of microcarriers (e.g., two or more microcarriers having a different shape, size, charge, or composition).

Non-limiting exemplary microcarriers that can be used in any of the methods described herein include CytoPore™ 1 and CytoPore™ 2 (available from GE Healthcare, Life Sciences, Piscataway, N.J.). Additional examples of microcarriers that can be used in any of the methods described herein are publicly available and known in the art.

Shake Tubes

The shake tube can be sterile and have a volume between about 2 mL to about 500 mL (e.g., a 2-mL, 4-mL, 5-mL, 10-mL, 15-mL, 20-mL, 25-mL, 50-mL, 75-mL, 100-mL, 150-mL, 200-mL, 250-mL, 300-mL, 350-mL, 400-mL, 450-mL, or 500-mL shake tube. The shake tube can have a volume, for example, of about 2 mL to about 200 mL, about 10 mL to about 200 mL, about 2 mL to about 100 mL, about 20 mL to about 200 mL, about 20 mL to about 100 mL, about 2 mL to about 15 mL, about 2 mL to about 25 mL, about 2 mL to about 50 mL, about 10 mL to about 50 mL, about 5 mL to about 25 mL, about 25 mL to about 50 mL, about 2 mL to about 15 mL, about 3 mL to about 20 mL, about 3 mL to about 15 mL, about 2 mL to about 250 mL, about 2 mL to about 300 mL, about 2 mL to about 400 mL, about 2 mL to about 450 mL, about 10 mL to about 250 mL, about 10 mL to about 350 mL, about 10 mL to about 400 mL, about 10 mL to about 450 mL, about 20 mL to about 250 mL, about 20 mL to about 350 mL, about 20 mL to about 400 mL, about 20 mL to about 450 mL, about 50 mL to about 100 mL, about 50 mL to about 150 mL, about 50 mL to about 250 mL, about 50 mL to about 300 mL, about 50 mL to about 350 mL, about 50 mL to about 400 mL, about 50 mL to about 450 mL, about 100 mL to about 150 mL, about 150 mL to about 200 mL, about 200 mL to about 250 mL, about 250 mL to about 350 mL, about 300 mL to about 400 mL, or about 350 mL to about 450 mL. Non-limiting examples of shake tubes are Tubespin® shake tubes (TPP Techno Plastic Products AG, Trasadingen, Switzerland).

The shake tube can include at least one gas permeable surface (e.g., at least one surface having a gas permeable membrane which may also act as a sterile barrier) and/or at least one vented cap. A shake tube may have on its outer surface a structure that allows the shake tube to be stably placed in a tissue culture incubator (e.g., a rotary incubator).

The interior surface of the shake tube may have at least one coating (e.g., at least one coating of gelatin, collagen, poly-L-ornithine, polystyrene, and laminin). The shake tube can be, for example, a TubeSpin® shake tube available from Techno Plastic Products AG, Trasadingen, Switzerland, the shake tubes available from Sartorius, AG, Germany, and sterile Becton Dickinson (BD) Falcon tubes. Additional examples of shake tubes (e.g., different shapes and dimensions of shake tubes) and interior surface coatings of shake tubes are known in the art and can be used in the present methods.

Agitation

The methods described herein involve the agitation of the culture containing the mammalian cell, a plurality of microcarriers, and the first and/or second liquid culture medium. The agitation can occur at a frequency of at about 120 RPM to about 240 RPM, (e.g., about 125 RPM to about 180 RPM, about 125 RPM to about 175 RPM, about 130 RPM to about 180 RPM, about 130 RPM to about 170 RPM, about 135 RPM to about 170 RPM, about 135 RPM to about 165 RPM, about 140 RPM to about 165 RPM, about 140 RPM to about 160 RPM, about 130 RPM to about 170 RPM, about 120 RPM to about 150 RPM, about 125 RPM to about 155 RPM, about 130 RPM to about 160 RPM, about 140 RPM to about 170 RPM, about 145 RPM to about 175 RPM, about 150 RPM to about 180 RPM, about 120 RPM to about 150 RPM, about 150 RPM to about 180 RPM, about 120 RPM to about 230 RPM, about 120 RPM to about 220 RPM, about 120 RPM to about 210 RPM, about 120 RPM to about 200 RPM, about 120 RPM to about 190 RPM, about 130 RPM to about 200 RPM, or about 120 RPM to about 180 RPM) (e.g., in an incubator, such as a shake incubator with throw (orbit) diameter from about 3 mm to about 50 mm).

As can be appreciated in the art, the level of agitation (e.g., RPM speed) can be varied depending upon the size and shape of the shake tube (e.g., the diameter of the shake tube), the throw (orbit) diameter of the incubator that is used to perform the agitation, and the average size, shape, density, and concentration of the plurality of microcarriers. For example, a smaller throw (orbit) diameter can require a higher level of agitation (e.g., a higher RPM speed), while a larger throw (orbit) diameter can require a lower level of agitation (e.g., a lower RPM speed) to achieve the conditions necessary to achieve optimal viable cell density and recombinant protein production. For example, for a throw (orbit) diameter of, e.g., 9 mm, the frequency of agitation can be greater than 180 RPM (e.g., between about 180 RPM to about 240 RPM). In another example, a shake tube having a larger diameter can require a lower RPM speed, while a shake tube having a smaller diameter can require a higher RPM speed to achieve the conditions necessary to achieve optimal viable cell density and recombinant protein production. The frequency of agitation can be varied depending on cell culture conditions, e.g., the concentration, density, and/or the size and/or surface shape of the microcarriers. As one skilled in the art can appreciate, if microcarriers present in the first and/or second liquid culture medium (e.g., the first and/or second liquid culture medium used in the first, second, and third time periods) have a high mass, a high density, a large outer surface area, or a relatively high velocity, the sheer forces generated by such microcarriers can have a negative impact on cell viability and recombinant protein production in the culture. In addition, those in the art can appreciate that the rate of agitation should be high enough to avoid substantial and/or undesirable settling of the microcarriers on the bottom of shake tube.

In some embodiments, the incubating is performed using a rotary incubator with a throw (orbit) diameter of between about 25 mm to about 50 mm and an agitation of between about 120 RPM to about 180 RPM (e.g., about 125 RPM to about 180 RPM, about 125 RPM to about 175 RPM, about 130 RPM to about 180 RPM, about 130 RPM to about 170 RPM, about 135 RPM to about 170 RPM, about 135 RPM to about 165 RPM, about 140 RPM to about 165 RPM, about 140 RPM to about 160 RPM, about 130 RPM to about 170 RPM, about 120 RPM to about 150 RPM, about 125 RPM to about 155 RPM, about 130 RPM to about 160 RPM, about 140 RPM to about 170 RPM, about 145 RPM to about 175 RPM, about 150 RPM to about 180 RPM, about 120 RPM to about 150 RPM, about 150 RPM to about 180 RPM, about 120 RPM to about 150 RPM, or about 150 RPM to about 180 RPM). In some embodiments, the incubating is performed using a rotary incubator with a throw (orbit) diameter of about 3 mm to about 25 mm and an agitation of about 120 RPM to about 240 RPM (e.g., about 125 RPM to about 180 RPM, about 125 RPM to about 175 RPM, about 130 RPM to about 180 RPM, about 130 RPM to about 170 RPM, about 135 RPM to about 170 RPM, about 135 RPM to about 165 RPM, about 140 RPM to about 165 RPM, about 140 RPM to about 160 RPM, about 130 RPM to about 170 RPM, about 120 RPM to about 150 RPM, about 125 RPM to about 155 RPM, about 130 RPM to about 160 RPM, about 140 RPM to about 170 RPM, about 145 RPM to about 175 RPM, about 150 RPM to about 180 RPM, about 120 RPM to about 150 RPM, about 150 RPM to about 180 RPM, about 120 RPM to about 230 RPM, about 120 RPM to about 220 RPM, about 120 RPM to about 210 RPM, about 120 RPM to about 200 RPM, about 120 RPM to about 190 RPM, about 130 RPM to about 200 RPM, or about 120 RPM to about 180 RPM).

Agitation can be performed, e.g., using rotary circular shaking at a frequency of about 120 RPM to about 240 RPM (e.g., about 125 RPM to about 180 RPM, about 125 RPM to about 175 RPM, about 130 RPM to about 180 RPM, about 130 RPM to about 170 RPM, about 135 RPM to about 170 RPM, about 135 RPM to about 165 RPM, about 140 RPM to about 165 RPM, about 140 RPM to about 160 RPM, about 130 RPM to about 170 RPM, about 120 RPM to about 150 RPM, about 125 RPM to about 155 RPM, about 130 RPM to about 160 RPM, about 140 RPM to about 170 RPM, about 145 RPM to about 175 RPM, about 150 RPM to about 180 RPM, about 120 RPM to about 150 RPM, about 150 RPM to about 180 RPM, about 120 RPM to about 230 RPM, about 120 RPM to about 220 RPM, about 120 RPM to about 210 RPM, about 120 RPM to about 200 RPM, about 120 RPM to about 190 RPM, about 130 RPM to about 200 RPM, or about 120 RPM to about 180 RPM). Alternatively or in addition, the shake tube can be agitated using a rotary ellipsoidal shaking, or horizontal and/or vertical tilting of the shake tube. The agitation can be performed continuously or periodically.

The agitation can be performed using a humidified atmosphere controlled incubator (e.g., at a humidity of about or greater than 20%, e.g., about or greater than 30%, 40%, 50%, 60%, 70%, 75%, 80%, 85%, 90%, or 95%, or a humidity of 100%) with a mechanical device that provides the agitation of one or more of the shake tubes containing the mammalian cell, the plurality of microcarriers, and a liquid culture medium (e.g., the first and/or second liquid culture medium, and the first and/or second liquid culture medium used in one or more of the first, second, and third time periods).

Reactor Angle

The shake tube can be incubated at a reactor angle of about 25 degrees to about 90 degrees (e.g., about 25 degrees to about 55 degrees, about 25 degrees to about 90 degrees, about 35 degrees to about 90 degrees, about 45 degrees to about 90 degrees, or about 35 to about 65 degrees) from horizontal. For example, the shake tube can be placed at a reactor angle of about 60 degrees to about 85 degrees from horizontal, about 70 degrees to about 85 degrees from horizontal, about 25 degrees to about 60 degrees, about 25 degrees to about 55 degrees, about 30 degrees to about 55 degrees from horizontal, about 40 degrees to about 55 degrees horizontal, or about 40 degrees to about 50 degrees from horizontal. The shake tube may be placed at a reactor angle of about 45 degrees from horizontal to about 50 degrees from horizontal, or from about 40 degrees from horizontal to about 45 degrees from horizontal. The shake tube may be placed in a device that specifically and securely positions the shake tube at a reactor angle of about 25 degrees to about 90 degrees from horizontal (e.g., specifically positions the container at a reactor angle of about 25 degrees to about 90 degrees, about 35 degrees to about 90 degrees, about 45 degrees to about 90 degrees, about 35 degrees to about 65 degrees, or about 40 degrees to about 55 degrees from horizontal). The positioning of the shake tube can be performed using any means known in the art, e.g., through the use of a brace or a locking element.

Temperature

The culturing methods described herein can be performed at a temperature of about 32° C. to about 39° C. For example, in some methods the shake tube can be incubated at a temperature of about 37° C. from the beginning to the end of the culture run. Some examples of the methods described herein include a first time period during which the shake tube is incubated at a temperature of about 35° C. to about 39° C., a second time period during which the shake tube is incubated at about 32° C. to about 39° C., and third time period during which the shake tube is incubated at about 35° C. to about 39° C. Skilled practitioners will appreciate that the temperature can be changed at specific time point(s) in the culturing method (e.g., during one or more of the first time period, the second time period, and the third time period), e.g., on an hourly or daily basis. For example, the temperature can be changed or shifted (e.g., increased or decreased) at about one day, two days, three days, four days, five days, six days, seven days, eight days, nine days, ten days, eleven days, twelve days, fourteen days, fifteen days, sixteen days, seventeen days, eighteen days, nineteen days, or about twenty days or more after the initial seeding of the shake tube with the mammalian cell) or at any time point within the first, second, and/or third time periods described herein. For example, the temperature can be shifted upwards (e.g., a change of up to or about 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or 10.0° C.). For example, the temperature can be shifted downwards (e.g., a change of up to or about 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or 10° C.).

Culture Medium Removal and Replacement

The methods described herein include removing from the shake tube a first volume of a first liquid culture medium (e.g., containing any concentration of mammalian cells and any recombinant protein, e.g., a first volume of a first liquid culture medium that is substantially free of cells and/or microcarriers), and adding to the shake tube a second volume of a second liquid culture medium, wherein the first volume and the second volume are about equal. Removal and adding can be performed simultaneously or sequentially, or a combination of the two. Further, removal and adding can be performed continuously (e.g., at a rate that removes and replaces a volume of between 0.1% to 800% (e.g., between 1% and 700%, between 1% and 600%, between 1% and 500%, between 1% and 400%, between 1% and 350%, between 1% and 300%, between 1% and 250%, between 1% and 100%, between 100% and 200%, between 5% and 150%, between 10% and 50%, between 15% and 40%, between 8% and 80%, and between 4% and 30%) of the volume of the shake tube or the first liquid culture medium volume over any given time period (e.g., over a 24-hour period, over an incremental time period of about 1 hour to about 24 hours, or over an incremental time period of greater than 24 hours)) or periodically (e.g., once every third day, once every other day, once a day, twice a day, three times a day, four times a day, five times a day, or more than five times a day), or any combination thereof. Where performed periodically, the volume that is removed or replaced (e.g., within about a 24-hour period, within an incremental time period of about 0.1 hour to about 24 hours, or within an incremental time period of greater than 24 hours) can be, e.g., between 0.1% to 800% (e.g., between 1% and 700%, between 1% and 600%, between 1% and 500%, between 1% and 400%, between 1% and 300%, between 1% and 200%, between 1% and 100%, between 100% and 200%, between 5% and 150%, between 10% and 50%, between 15% and 40%, between 8% and 80%, and between 4% and 30%) of the volume of the shake tube or the first liquid culture medium volume. The first volume of the first liquid culture medium removed and the second volume of the second liquid culture medium added can in some instances be held approximately the same over each 24-hour period (or, alternatively, an incremental time period of about 0.1 hour to about 24 hours or an incremental time period of greater than 24 hours) over the entire or part of the culturing period. As is known in the art, the rate at which the first volume of the first liquid culture medium is removed (volume/unit of time) and the rate at which the second volume of the second liquid culture medium is added (volume/unit of time) can be varied. The rate at which the first volume of the first liquid culture medium is removed (volume/unit of time) and the rate at which the second volume of the second liquid culture medium is added (volume/unit of time) can be about the same or can be different.

Alternatively, the volume removed and added can change (e.g., gradually increase) over each 24-hour period (or alternatively, an incremental time period of between 0.1 hour and about 24 hours or an incremental time period of greater than 24 hours) during the culturing period. For example the volume of the first liquid culture medium removed and the volume of the second liquid culture medium added within each 24-hour period (or alternatively, an incremental time period of between about 1 hour and above 24 hours or an incremental time period of greater than 24 hours) over the culturing period can be increased (e.g., gradually or through staggered increments) over the culturing period from a volume that is between 0.5% to about 20% of the shake tube volume or the first liquid culture medium volume to about 25% to about 150% of the shake tube volume or the first liquid culture medium volume.

In some examples of the methods described herein, after the first 48 to 96 hours of the culture period, in each 24-hour period, the first volume of the first liquid culture medium removed (e.g., in the first, second, and/or third time period) and the second volume of the second liquid culture medium added (e.g., in the first, second, and/or third time period) is about 10% to about 95% (e.g., about 10% to about 20%, about 10% to about 20%, about 20% to about 30%, about 30% to about 40%, about 40% to about 50%, about 50% to about 60%, about 60% to about 70%, about 70% to about 80%, about 80% to about 90%, about 30% to about 80%, about 85% to about 95%, about 60% to about 80%, or about 70%) of the volume of the first liquid culture medium.

Skilled practitioners will appreciate that the first liquid culture medium and the second liquid culture medium can be the same type of media. In other instances, the first liquid culture medium and the second liquid culture medium can be substantially different. In some embodiments that include a first time period, second time period, and third time period, the first and second liquid culture media used in the first time period are a substantially different type of media compared to the first and second liquid culture media used in the second time period, and the first and second liquid culture media used in the second time period are the same type of media compared to the first and second liquid culture media used in the third time period. As can be recognized in the art, the first and second liquid culture media used in the first time period do not have to be exactly the same (as long as they are the same type of culture medium); any of the first and second liquid culture media used in the second time period and/or third time period do not have to be exactly the same (again, as long as they are the same type of medium and a substantially different media type from the first and second liquid culture medium used in the first time period).

The first volume of the first liquid culture medium can be removed, e.g., by centrifuging (e.g., slow-speed swinging bucket centrifugation) the shake tube or using any other automated system, and removing the first volume of the first liquid culture (e.g., a first volume of the first liquid culture medium that is substantially free of cells and/or microcarriers) from the supernatant. Alternatively or in addition, the first volume of the first liquid culture medium can be removed by seeping or gravity flow of the first volume of the first liquid culture medium through a sterile membrane with a molecular weight cut-off that excludes the mammalian cell and/or microcarriers. Alternatively or in addition, the first volume of the first liquid culture medium can be removed by stopping or significantly decreasing the rate of agitation for a period of at least 10 seconds (e.g., at least 30 seconds, 40 seconds, 50 seconds, 1 minutes, 2 minutes, 3 minutes, 4 minutes, 5 minutes, 10 minutes, 15 minutes, 20 minutes, 25 minutes, 30 minutes, 40 minutes, 50 minutes, or 1 hour) and removing or aspirating the first volume of the first liquid culture medium from the top of the shake tube (e.g., removal from a part of the liquid culture medium where the microcarriers have not settled due to gravitational force). The shake tube may be placed in an incubator during the period in which the agitation is ceased. One skilled in the art will understand that the shake tube may be removed from the incubator for a short period of time (e.g., less than 30 minutes, 20 minutes, 15 minutes, 10 minutes, 8 minutes, 6 minutes, 4 minutes, 2 minutes, or 1 minute) while the first liquid culture medium is removed from the shake tube.

The second volume of the second liquid culture medium can be added to the first liquid culture medium, e.g., by perfusion pump. The second liquid culture medium can be added to the first liquid culture medium manually (e.g., by pipetting the second volume of the second liquid culture medium directly onto the first liquid culture medium) or in an automated fashion.

In some instances, removing the first volume of the first liquid culture medium (e.g., a first volume of the first liquid culture medium that is substantially free of mammalian cells and/or microcarriers) and adding to the first liquid culture medium a second volume of the second liquid culture medium does not occur within at least 1 hour (e.g., within 2 hours, within 3 hours, within 4 hours, within 5 hours, within 6 hours, within 7 hours, within 8 hours, within 9 hours, within 10 hours, within 12 hours, within 14 hours, within 16 hours, within 18 hours, within 24 hours, within 36 hours, within 48 hours, within 72 hours, within 96 hours, or after 96 hours) of the seeding of the shake tube with a mammalian cell.

$CO_2$

Methods described herein can further include incubating the shake tube in an atmosphere containing at most or about 1% to 15% $CO_2$ (e.g., at most or about 14% $CO_2$, 12% $CO_2$, 10% $CO_2$, 8% $CO_2$, 6% $CO_2$, 5% $CO_2$, 4% $CO_2$, 3% $CO_2$, 2% $CO_2$, or at most or about 1% $CO_2$). Moreover, any of the methods described herein can include incubating the shake tube in a humidified atmosphere (e.g., at least or about 20%, 30%, 40%, 50%, 60%, 70%, 85%, 80%, 85%, 90%, or at least or about 95% humidity, or about 100% humidity).

Exemplary Devices

Non-limiting examples of devices that can be used to perform the culturing methods described herein include: Appropriate Technical Resources (Maryland, USA) distributes INFORS Multiron shake incubator (INFORS; Basel, Switzerland), and Kuhner shake incubator (Kuhner AG; Basel, Switzerland). Non-limiting examples of devices that can be used to perform the culturing methods include a rotary incubator with a throw (orbit) diameter of between about 3 mm to about 50 mm (e.g., between about 1 mm and about 25 mm, or between about 25 mm and about 50 mm). Additional examples of shake incubators are known in the art.

Methods of Producing a Recombinant Protein

Also provided herein are methods of producing a recombinant protein, which include culturing a cell that is capable of producing the recombinant protein using a method described herein. Following performance of the method, the recombinant protein can be recovered from the mammalian cell (e.g., the mammalian cell that is attached to the microcarrier) and/or from the first or second culture medium (e.g., the first and/or second liquid culture medium used in one or more of the first, second, and third time periods). In some embodiments, the recombinant protein is recovered from the first and/or second liquid culture medium at any given time point during the culturing method (e.g., recovered from the first and/or second liquid culture medium on one or more of days 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 of culture, or after more than 100 days of culture, or at any time point during one or more of the first time period, the second time period, and the third time period).

Skilled practitioners will appreciate that any of the various culture parameters (e.g., shake tubes, volumes, rates or frequencies of replacing culture volumes, agitation frequencies, type of microcarrier, temperatures, media, and $CO_2$ concentrations) can be used in any combination to perform these methods. Further, any of the mammalian cells described herein or known in the art can be used to produce a recombinant protein.

A nucleic acid encoding a recombinant protein can be introduced into a mammalian cell using a wide variety of methods known in molecular biology and molecular genetics. Non-limiting examples include transfection (e.g., lipofection), transduction (e.g., lentivirus, adenovirus, or retrovirus infection), and electroporation. In some instances, the nucleic acid that encodes a recombinant protein is not stably integrated into a chromosome of the mammalian cell (transient transfection), while in others the nucleic acid is integrated. Alternatively or in addition, the nucleic acid encoding a recombinant protein can be present in a plasmid and/or in a mammalian artificial chromosome (e.g., a human artificial chromosome). Alternatively or in addition, the nucleic acid can be introduced into the cell using a viral vector (e.g., a lentivirus, retrovirus, or adenovirus vector). The nucleic acid can be operably linked to a promoter sequence (e.g., a strong promoter, such as a β-actin promoter and CMV promoter, or an inducible promoter). A vector containing the nucleic acid can, if desired, also contain a selectable marker (e.g., a gene that confers hygromycin, puromycin, or neomycin resistance to the mammalian cell).

In some instances, the recombinant protein is a secreted protein and is released by the mammalian cell into the extracellular medium (e.g., the first and/or second liquid culture medium, e.g., the first and/or second liquid culture medium used in one or more of the first, second, and third time periods). For example, a nucleic acid sequence encoding a soluble recombinant protein can contain a sequence that encodes a secretion signal peptide at the N- or C-terminus of the recombinant protein, which is cleaved by an enzyme present in the mammalian cell, and subsequently released into the extracellular medium (e.g., the first and/or second liquid culture medium, or the first and/or second liquid culture medium used in one or more of the first, second, and third time periods). In other instances, the recombinant protein is a soluble protein that is not secreted, and the recombinant protein is recovered from within the mammalian cell (e.g., from within the mammalian cell that is attached to the microcarrier, e.g., recovered from the mammalian cell attached to the microcarrier after it has been unattached from the microcarrier).

Non-limiting examples of recombinant proteins that can be produced by the methods provided herein include immunoglobulins (including light and heavy chain immunoglobulins, antibodies, or antibody fragments (e.g., any of the antibody fragments described herein), enzymes (e.g., a galactosidase (e.g., an alpha-galactosidase), Myozyme, or Cerezyme), proteins (e.g., human erythropoietin, tumor necrosis factor (TNF), or an interferon alpha or beta), or immunogenic or antigenic proteins or protein fragments (e.g., proteins for use in a vaccine). In some embodiments, the recombinant protein is an engineered antigen-binding polypeptide that contains at least one multifunctional recombinant protein scaffold (see, e.g., the recombinant antigen-binding proteins described in Gebauer et al., Current Opin. Chem. Biol. 13:245-255, 2009; and U.S. Patent Application Publication No. 2012/0164066 (herein incorporated by reference in its entirety)). Non-limiting examples of recombinant proteins that are antibodies include: panitumumab, omalizumab, abagovomab, abciximab, actoxumab, adalimumab, adecatumumab, afelimomab, afutuzumab, alacizumab, alacizumab, alemtuzumab, alirocumab, altumomab, amatuximab, anatumomab, apolizumab, atinumab, tocilizumab, basilizimab, bectumomab, belimumab, bevacizumab, biciromab, canakinumab, cetuximab, daclizumab, densumab, eculizumab, edrecolomab, efalizumab, efungumab, ertumaxomab, etaracizumab, golimumab, infliximab, natalizumab, palivizumab, panitumumab, pertuzumab, ranibizumab, rituximab, tocilizumab, and trastuzumab. Additional examples of therapeutic antibodies that can be produced by the methods described herein are known in the art. Additional non-limiting examples of recombinant proteins that can be produced by the present methods include: alglucosidase alfa, laronidase, abatacept, galsulfase, lutropin alfa, antihemophilic factor, agalsidase beta, interferon beta-la, darbepoetin alfa, tenecteplase, etanercept, coagulation factor IX, follicle stimulating hormone, interferon beta-la, imiglucerase, dornase alfa, epoetin alfa, and alteplase.

A secreted, soluble recombinant protein can be recovered from the liquid culture medium (e.g., the first and/or second liquid culture medium, e.g., the first and/or second liquid culture medium used in one or more of the first, second, and third time periods) by removing or otherwise physically separating the liquid culture medium from microcarriers and their associated mammalian cells. A variety of different methods for removing liquid culture medium from mammalian cells are known in the art, including, for example, centrifugation, filtration, pipetting, and/or aspiration. The secreted recombinant protein can then be recovered and further purified from the liquid culture medium using a variety of biochemical techniques including various types of chromatography (e.g., affinity chromatography, molecular sieve chromatography, cation exchange chromatography, or anion exchange chromatography) and/or filtration (e.g., molecular weight cut-off filtration).

To recover an intracellular recombinant protein, the mammalian cell (e.g., the mammalian cell attached to the microcarrier) can be lysed. In some examples, the mammalian cell is released from the surface of the microcarrier before it is lysed. Methods for releasing an adherent cell from the surface of a microcarrier are known in the art (e.g., vortexing or agitation). In other examples, the mammalian cell is lysed while it is still attached to the microcarrier (e.g., using any of the exemplary methods listed below).

A wide variety of methods for lysing mammalian cells are known in the art, including, for example, sonication and/or detergent, enzymatic, and/or chemical lysis. A recombinant protein can be purified from a mammalian cell lysate using a variety of biochemical methods known in the art, typically starting with a step of centrifugation to remove the cellular debris, and then one or more additional steps (e.g., one or more types of chromatography (e.g., affinity chromatography, molecular sieve chromatography, cation exchange chromatography, or anion exchange chromatography) and/or filtration (e.g., molecular weight cut-off filtration)).

In some embodiments, the recovered recombinant protein is at least or about 50% pure by weight, e.g., at least or about 55% pure by weight, at least 60% pure by weight, at least 65% pure by weight, at least 70% pure by weight, at least 75% pure by weight, at least 80% pure by weight, at least 85% pure by weight, at least 90% pure by weight, at least 95% pure by weight, at least 96% pure by weight, at least 97% pure by weight, at least 98% pure by weight, or at least or about 99% pure by weight, or greater than 99% pure by weight.

In some embodiments, the recovered recombinant protein is a recombinant human protein that has one or more different biophysical properties as compared to the same native protein in a human (e.g., differences in the type or amount of glycosylation, differences in phosphorylation, differences in acylation, differences in metallation or metal stoichiometry, and/or differences in cofactor binding).

Also provided herein is a recombinant protein produced by any of the methods described herein.

Methods for Testing a Manufacturing Process

Also provided herein are methods for testing a manufacturing process for making a recombinant protein. These methods include performing a method of producing a recombinant protein described herein and, during the method and/or afterward, detecting or measuring at least one (e.g., two, three, four, five, six, seven, eight, nine, ten, eleven, or twelve) culture readout (e.g., the recombinant protein in the cell or in the first and/or second culture medium (e.g., the first and/or second liquid culture medium used in one or more of the first, second, and third time periods), glucose consumption, viable cell concentration, lactate production, volumetric productivity, specific productivity, lactate yield from glucose, glutamine concentration, glutamate concentration, pH of culture medium, partial pressure or concentration of dissolved $CO_2$, partial pressure or concentration of dissolved $O_2$, metabolite mass transfer, and metabolite mass balance); and comparing the at least one culture readout to a reference level of the at least one (e.g., two, three, four, five, six, seven, eight, nine, ten, eleven, or twelve) culture readout (e.g., a reference level of the recombinant protein in the cell or in the first and/or second culture medium (e.g., the first and/or second liquid culture medium used in one or more of the first, second, and third time periods), glucose consumption, viable cell concentration, lactate production, volumetric productivity, specific productivity, lactate yield from glucose, glutamine concentration, glutamate concentration, pH of culture medium, concentration or partial pressure of dissolved $CO_2$, concentration or partial pressure of dissolved $O_2$, metabolite mass transfer, and metabolite mass balance).

Skilled practitioners will appreciate that any of the various culture parameters (e.g., shake tubes, volumes, type of microcarrier, rates or frequencies of replacing culture volumes, agitation frequencies, temperatures, media, and $CO_2$ exposure) described herein can be used in any combination to perform these methods. Further, any of the mammalian cells described herein or known in the art can be used in the methods.

The reference level of the at least one culture readout (e.g., level of recombinant protein in the cell or in the first and/or second culture medium (e.g., the first and/or second liquid culture medium used in one or more of the first, second, and third time periods), glucose consumption, viable cell concentration, lactate production, volumetric productivity, specific productivity, lactate yield from glucose, glutamine concentration, glutamate concentration, pH of culture medium, concentration or partial pressure of dissolved $CO_2$, concentration or partial pressure of dissolved $O_2$, metabolite mass transfer, and metabolite mass balance) can be a level produced using a different culturing method, e.g., a culturing method that utilizes at least one different culture parameter (e.g., a different first and/or second liquid culture medium (e.g., a different first and/or second liquid culture medium in one or more of the first, second, or third time periods), a different mammalian cell, a different frequency and/or type of agitation, a different type or concentration of microcarrier, a different batch re-feed or perfusion rate (e.g., 10% to 95% of the shake tube volume or the first liquid culture medium volume over each 24-hour time period after the first 48 to 96 hours of culture), and any of the other culture parameters described herein).

The methods described herein can be used to test the effect of any component or feature of a manufacturing process. For example, the method described herein can be used to test the effect of different raw materials, microcarriers, agitation levels, shake tubes, anti-clumping agents, culture media (e.g., chemically-defined culture media), or nutrient elements or compounds on the at least one culture readout (e.g., any of the culture readouts described herein, e.g., the effect on recombinant protein production and/or mammalian cell growth). For example, provided herein are methods of testing the efficacy of a first or second liquid culture medium, a raw ingredient or supplement present in a first or second liquid culture medium, or a source of a mammalian cell for use in a method of producing a recombinant protein that include providing a shake tube containing a mammalian cell disposed in a first liquid culture medium, wherein the first liquid culture medium occupies, e.g., about 10% to about 30% of the volume of the shake tube, and contains a plurality of microcarriers at a concentration of about 1.0 g/L to about 15.0 g/L; incubating the shake tube for a period of time at about 32° C. to about 39° C. and with a rotary agitation of about 120 revolutions per minute (RPM) to about 240 RPM; and after about the first 48 to 96 hours of the period of time, continuously or periodically removing a first volume of the first liquid culture medium and adding to the first liquid culture medium a second volume of a second liquid culture medium, wherein the first and second volumes are about equal; detecting or determining at least one culture readout (e.g., any of the culture readouts described herein, e.g., the recombinant protein in the cell or in the first and/or second culture medium); comparing the at least one culture readout to a reference level of the at least one culture readout (e.g., any of the culture readouts described herein, e.g., recombinant protein in the cell or in the first and/or second liquid culture medium) produced by a different culturing method that uses one or more of a different first or second liquid culture medium, a different raw ingredient or supplement present in the first or second liquid culture medium, or a different source of a mammalian cell; and identifying the first or second liquid culture medium, the raw ingredient or supplement present in the first or second liquid culture medium, or the source of the mammalian cell that is associated with beneficial change (e.g., increase or decrease) in the at least one culture readout (e.g., an increased amount of recombinant protein) as compared to the reference level as being efficacious for use in a method of producing a recombinant protein. For example, an increase in recombinant protein level, an increase in viable cell concentration, an increase in volumetric productivity, and an increase in glucose consumption compared to the reference level indicates that the first or second liquid culture medium, the raw ingredient or supplement present in a first or second liquid culture medium, or the source of the mammalian cell are efficacious for use in a method of producing a recombinant protein.

The methods described herein can also be used to test the effect of changing any of the various cell culture parameters described herein or known in the art (e.g., the volume or shape of a shake tube, the frequency of agitation, the sheer force generated by the plurality of microcarriers in the first and/or second liquid culture medium, the culture seeding density, the pH of the first and/or second liquid culture medium (e.g., the pH of the first and/or second liquid culture medium used in one or more of the first, second, or third time periods), dissolved $O_2$ concentration or partial pressure, the inner surface coating of the shake tube, one or more of the concentration, size, shape, surface properties, density, and porosity of the microcarriers, the various ingredients within a liquid culture medium (e.g., the first and/or second liquid culture medium, e.g., the first and/or second liquid culture medium used in one or more of the first, second, and third time periods), the amount and/or type of agitation, the mammalian cell type or line, dissolved $CO_2$ concentration or partial pressure, the temperature, the volume of liquid culture medium (e.g., the volume of the first and/or second liquid culture medium), and/or the rate or frequency of removing the first volume of the first liquid culture medium and adding the second volume of the second liquid culture medium to the first culture medium (e.g., the rate or frequency of removing the first volume of the first culture medium and adding the second volume of the second liquid culture medium in one or more of the first, second, and third time periods). The methods can also be used to test the quality of water used to prepare the liquid culture medium (e.g., the first and/or second liquid culture medium, e.g., the first and/or second liquid culture medium used in one or more of the first, second, and third time periods) and/or the effect of different trace metals in the liquid culture medium on at least one culture readout on at least one culture readout (e.g., any of the culture readouts described herein, e.g., the effect on recombinant protein production and/or mammalian cell growth). The methods can also be used to test the effect of a growth factor or growth hormone (e.g., the effect of the presence of a growth factor or growth hormone in the first time period) on at least one culture readout (e.g., any of the culture readouts described herein, e.g., the effect on recombinant protein production and/or mammalian cell growth). The method can also be used to test filtration processes and filters used to prepare the first and/or second liquid culture medium (e.g., the first and/or second liquid culture medium used in one or more of the first, second, and third time periods). The method can also be used to test liquid culture medium stability and the effect of a liquid culture medium on at least one culture readout (e.g., any of the culture readouts described herein, e.g., the effect on recombinant protein production and/or mammalian cell growth). The method can also be used to screen various recombinant cells lines and cell banks for their ability to produce a desired recombinant protein (e.g., a desired secreted therapeutic protein). As noted herein, the method can also be used to screen any cell culture process parameter, including but not limited to, the type and frequency of agitation, sheer force generated by the microcarriers, perfusion rate and volume, culture seeding density, and others.

The method described herein can also be used to test for the presence of a contaminant in a first or second liquid culture medium, a raw material used to generate a first or second liquid culture medium, or a source of a mammalian cell. For example, provided herein are methods of testing for the presence of a contaminant in a first or second liquid culture medium, raw materials used to generate a first or second liquid culture medium, or a source of a mammalian cell that include providing a shake tube containing a mammalian cell disposed in a first liquid culture medium, wherein the first liquid culture medium occupies about, e.g., 10% to about 30% of the volume of the shake tube, and contains a plurality of microcarriers at a concentration of about 1.0 g/L to about 15.0 g/L; incubating the shake tube for a period of time at about 32° C. to about 39° C. and with a rotary agitation of about 120 revolutions per minute (RPM) to about 240 RPM; and after about the first 48 to 96 hours of the period of time, continuously or periodically removing a first volume of the first liquid culture medium and adding to the first liquid culture medium a second volume of a second liquid culture medium, wherein the first and second volumes are about equal; detecting or determining at least one culture readout (e.g., any of the culture readouts described herein, e.g., the recombinant protein in the cell or in the first and/or second culture medium); comparing the at least one culture readout to a reference level of the at least one culture readout (e.g., any of the culture readouts described herein, e.g., amount of recombinant protein present in the cell or in the first and/or second culture medium) produced by a different culturing method that uses one or more of a different first or second liquid culture medium, different raw materials to generate the first or second liquid culture medium, or a different source of the mammalian cell; and identifying the first or second liquid culture medium, the raw materials used to generate the first or second liquid culture medium, or the source of a mammalian cell as containing a contaminant when the level of the at least one culture parameter is detrimentally changed (e.g., increased or decreased) compared to the reference level. For example, a decrease in recombinant protein production (e.g., a decrease in recombinant protein in the cell or in the first and/or second culture medium), volumetric productivity, or viable cell concentration as compared to the reference level is a detrimental change that indicates the presence of a contaminant in the first or second liquid culture medium, a raw material used to generate the first or second liquid culture medium, or the source of the mammalian cell. Some methods further include one or more assays to determine the identity of the contaminant present in the first or second liquid culture medium, the raw material used to generate the first or second liquid culture medium, or the source of the mammalian cell. The contaminant can be a biological contaminant (e.g., a mycobacterium, a fungus, a bacterium, a virus, or an undesired mammalian cell). For example, the contaminant can be a vesivirus. The contaminant can be an inorganic contaminant. The contaminant can also be a physically uncharacterized substance.

The methods can used to conduct high throughput cell culture experiments to perform a design-of-experiment (DOE) or a quality-by-design (QBD) optimization of cell culturing methods. For example, provided herein are methods of optimizing a manufacturing process of producing a recombinant protein that include providing a shake tube containing a mammalian cell disposed in a first liquid culture medium, wherein the first liquid culture medium occupies, e.g., about 10% to about 30% of the volume of the shake tube, and contains a plurality of microcarriers at a concentration of about 1.0 g/L to about 15.0 g/L; incubating the shake tube for a period of time at about 32° C. to about 39° C. and with a rotary agitation of about 120 revolutions per minute (RPM) to about 240 RPM; and after about the first 48 to 96 hours of the period of time, continuously or periodically removing a first volume of the first liquid culture medium and adding to the first liquid culture medium a second volume of a second liquid culture medium, wherein the first and second volumes are about equal; detecting at least one culture readout (e.g., any of the culture readouts described herein, e.g., amount of recombinant protein in the cell or in the first and/or second culture medium); comparing the at least one culture readout to a reference level of the at least one culture readout (e.g., any of the culture readouts described herein, e.g., amount of recombinant protein present in the cell or in the first and/or second culture medium)

produced by a different culturing method; and identifying and removing or altering in a manufacturing process any culture components or parameters that are associated with a detrimental change (e.g., increase or decrease) in the at least one culture readout (e.g., any of the culture readouts described herein, e.g., amount of recombinant protein produced) as compared to the reference level of the at least one culture readout (e.g, any of the culture readouts described herein, e.g., recombinant protein produced), or identifying and adding to a manufacturing process any culture components or parameters that are associated with a beneficial change (e.g., increase or decrease) in the at least one culture readout (e.g., any of the culture readouts described herein, e.g., amount of recombinant protein produced) as compared to the reference level of the at least one culture readout (e.g., any of the culture readouts described herein, e.g., recombinant protein produced). For example, an increase in the amount of recombinant protein produced, volumetric productivity, specific productivity, or viable cell concentration is a beneficial change in a culture readout, and a decrease in the amount of recombinant protein produced, volumetric productivity, specific productivity, or viable cell concentration is a detrimental change in a culture readout. In some instances, the method is used to identify in a high throughput fashion, optimized cell culture conditions that can be used for up-scaled (e.g., bioreactor) production of a recombinant protein.

In any of the methods described in this section, the reference level of the at least one culture readout can be from a larger-scale culture (e.g., a perfusion bioreactor, e.g., a 2000-L perfusion bioreactor, 40-L perfusion bioreactor, or a 12-L perfusion bioreactor). In some embodiments of any of the methods described in this section, the mammalian cell is cultured in a shake tube using any of the methods described herein over the same time period that a larger-scale culture is performed (cultured in parallel). For example, the inoculum used to inoculate the shake tube in any of the methods described herein is also used to inoculate a larger-scale perfusion bioreactor at approximately the same time.

In one embodiment, the inoculum that is used to seed the shake tube is obtained from a larger-scale culture (e.g., a larger-scale perfusion bioreactor). For example, an aliquot from a larger-scale culture (e.g., an aliquot from a larger-scale perfusion bioreactor) is removed from the larger-scale culture at any time point (e.g., removed during the growth phase, the transition phase, or the harvest phase described herein) and used to inoculate the shake tube (e.g., used to start a satellite shake tube culture). An aliquot can be removed from the larger-scale culture during the growth phrase and used to inoculate or seed a shake tube containing a liquid culture medium and a plurality of microcarriers (e.g., as described herein), and the shake tube is then incubated under conditions that replicate or are similar to the growth phase conditions employed in the larger-scale culture. An aliquot can alternatively, or additionally, be removed from the larger-scale culture during the transition phase and used to inoculate or seed a shake tube containing a liquid culture medium and a plurality of microcarriers (e.g., as described herein), and the shake tube is then incubated under conditions that replicate or are similar to the transition phase conditions employed in the larger-scale culture. An aliquot can alternatively, or additionally, be removed from the larger-scale culture during the harvest phase and used to inoculate or seed a shake tube containing a liquid culture medium and a plurality of microcarriers (e.g., as described herein), and the shake tube is then incubated under conditions that replicate or are similar to the harvest phase conditions employed in the larger-scale culture. In any of these methods, one or more culture parameters can be altered in the methods used to culture the mammalian cell in the shake tube (as compared to the culture parameters or components used to culture the mammalian cell in the larger-scale culture), at least one culture readout is measured (e.g., one or more of any of the culture readouts described herein), and the at least one culture readout is compared to the at least one culture readout determined for the larger-scale culture. As can be appreciated by those in the art, these methods can be used to test the effect of a specific culture parameter or component on at least one culture readout during one or more specific phases in the culturing process (e.g., the effect of one or more culture parameters and/or culture component(s) on at least one culture readout during the growth, transition, and/or harvest phase).

In certain embodiment, these methods can also be performed to determine whether a contaminant is present in the larger-scale bioreactor, by determining or detecting at least one culture readout in the shake tube culture (e.g., one or more of any of the culture readouts described herein), comparing the at least one culture readout to a reference level of the at least one culture readout (e.g., a level of the at least one culture readout from a culture that is substantially free of contamination), and identifying the larger-scale bioreactor as containing a contaminant when the at least one culture readout in the shake tube culture as compared to the reference level of the at least one culture readout indicates that a contaminant is present in the shake tube. The contaminant can be, for example, a biological contaminant, such as a virus, a fungus, an undesired mammalian cell, or a bacterium, such as a mycobacterium. The contaminant can be, for example, a vesivirus.

EXAMPLES

The invention is further described in the following examples, which do not limit the scope of the invention described in the claims.

Example 1. Exemplary Culture Methods Using a Shake Tube and Microcarriers

Human α-galactosidase can be produced using established recombinant engineering techniques in a CHO cell line. The current manufacturing production of recombinant human α-galactosidase utilizes a 2000-L continuous perfusion microcarrier cell culture process technology. Typically the production cell culture process includes three phases: a growth, transition, and harvest phase. There is a demand for a high throughput cell culture process system that would accurately model the cell culture process conditions achieved in a 2000-L bioreactor cell culture process run.

Previous experiments demonstrated that a shake flask microcarrier batch-refeed cell culture process successfully replicates the cell growth and productivity achieved in a larger 2000-L bioreactor cell culture process run (U.S. Provisional Patent Application No. 61/768,085). Described in this Example is a shake tube microcarrier batch re-feed cell culture process that accurately simulates the recombinant human α-galactosidase 2000-L bioreactor perfusion cell culture process.

Materials and Equipment

Fabrazyme Cell Source

The human recombinant α-galactosidase-producing cells used in each cell culture process run were derived from the same cell bank, in order to ensure comparability between each cell culture process run. The cells are stably transformed with a nucleic acid that encodes a secreted form of human recombinant α-galactosidase. A growth medium (925 medium with 10% Dulbecco's bovine serum, pH 7.3, and 0.1% Pluronic F-68) was used during the cell bank culture expansion process.

Equipment

The following equipment was used to perform the experiments described in this Example: a Multitron Shaker Incubator (Appropriate Technical Resources, Inc., Model No. AG CH-4103), a Beckman Coulter Vi-Cell Cell Viability Analyzer (Beckman Coulter, Inc., Model XR), a YSI Biochemistry Analyzer (Yellow Springs Instruments, Inc. Model No. 2700 Select), and a Blood Gas Analyzer (Bayer AG, Model No. 248).

Experimental Design

The inoculum used for the exemplary shake tube microcarrier batch re-feed cell culture process runs was generated from a seed culture expansion of a thawed vial of recombinant human α-galactosidase-producing CHO cells. After five days of expansion of the thawed cells in 925 medium with 10% DBS, pH 7.3, and 0.1% Pluronic F-68, the seed culture was used to inoculate a shake tube (at a final concentration of $0.25\times10^6$ viable cells/mL in the shake tube) containing a sterilized microcarrier slurry (Cytopore II, final concentration of 1.5 g/L in the growth medium) and growth medium (925 medium with 6% DBS, pH 7.0, and 0.1% Pluronic F-68), which initiates the growth phase of the cell culture. The working volume for the shake tubes (50 mL total volume) was designed to be 7 mL. The cultures were maintained at 37° C. or 36° C., 80% relative humidity, and 5% $CO_2$. Three different frequencies of rotary agitation were tested for their capability to support and maintain cell growth and productivity: 120 RPM, 140 RPM, and 160 RPM. When each culture reached a target cell density of between $2.0\times10^6$ to $3.0\times10^6$ viable cells/mL, the transition phase was initiated by changing the liquid culture medium to a different production liquid culture medium (925 medium, pH 6.85-7.05, and 0.1% Pluronic F-68) and shifting the temperature to 32° C. After 5 days of the transition phase, the temperature was shifted back to 37° C. or 36° C., and the cultures were maintained with production liquid culture medium. Media exchange was initiated on the third day of the growth phase and was continued until the end of each cell culture process run, with a daily batch re-feed exchange of 70% of the initial volume of the liquid culture medium present in the shake tube at the start of the cell culture process run. On each day, starting on the third day of the growth phase, media exchange was performed by briefly stopping the agitation of the shake tube, placing the shake tube upright, allowing the microcarriers to settle to the bottom of the shake tube for about 1 minute to about 2 minutes, and removing from the shake tube a volume of the liquid culture medium that is 70% of the initial volume of the liquid culture medium present in the shake tube at the start of the culture when the culture medium is free of microcarriers by visual inspection, and then shortly thereafter, adding a volume of liquid culture medium that is substantially the same volume as the volume of liquid culture medium removed.

The inoculum used for the control shake flask microcarrier cell culture process runs was generated from a seed culture expansion of a thawed vial of the same recombinant human α-galactosidase-producing CHO cells used to inoculate the shake tube microcarrier cell culture process runs described in this Example. After five days of expansion of the thawed cells in 925 medium with 10% DBS, pH 7.3, and 0.1% Pluronic F-68, the seed culture was used to inoculate a shake flask (at a final concentration of $0.25\times10^6$ viable cells/mL in the shake flask) containing a sterilized microcarrier slurry (CytoPore2, GE Healthcare, Piscataway, N.J.; final concentration of 1.5 g/L; average size 200-280 μm; average pore size 30 μm) and growth medium (925 medium with 6% DBS, pH 7.0, and 0.1% Pluronic F-68), which initiates the growth phase of the cell culture. The cultures were maintained at 37° C. or 36° C., 95 RPM, 80% relative humidity, and 5% $CO_2$. When the culture reached a target cell density of between $2.5\times10^6$ to $3.0\times10^6$ viable cells/mL, the transition phase was initiated by changing the liquid culture medium to a different production liquid culture medium (925 medium, pH 6.85-7.05, and 0.1% Pluronic F-68) and shifting the temperature to 32° C. After 5 days of transition phase, the temperature was shifted back to 37° C. or 36° C., and the cultures were maintained with production liquid culture medium. Medium exchange was initiated on the third day of the growth phase and was continued until the end of culture, with a daily batch re-feed exchange of 70% of the initial volume of the liquid culture medium present in the shake flask at the start of the culture. On each day, starting on the third day of the growth phase, medium exchange was performed by briefly stopping the agitation of the shake flask, allowing the microcarriers to settle to the bottom of the shake flask in a biosafety hood. In some instances, the shake flask was placed in a rack which positions the shake flask at a 45 degree angle with respect to the horizon or the benchtop while the microcarriers settled to the bottom of the shake flask in order to improve medium exchange. After the microcarriers have settled to the bottom of the shake flask, a volume of liquid culture medium that is 70% of the initial volume of the liquid culture medium present in the shake flask is removed from the shake flask, and then shortly thereafter, a volume of liquid culture medium that is substantially the same volume as the volume of liquid culture medium removed is added to the shake flask.

A summary of the process conditions and sampling schedule for each shake tube cell culture process run and shake flask cell culture process run is provided in Table 1.

On pre-determined culture days, the following culture parameters were analyzed in each cell culture process run: viable and suspension cell density, pCO2, pO2, pH, and glucose, lactate, glutamine, and glutamate concentration. Viable cell concentration is a

TABLE 1

Summary of Cell Culture Process Run Conditions and Sampling Schedule.

| | | Shake Flasks | Shake Tubes |
|---|---|---|---|
| Process Condition | Working Volume | 60 mL | 7 mL |
| | Vessel Volume | 250 mL | 50 mL |
| | Incubator Shaking Speed | 95 RPM | 120, 140, 160 RPM |
| Sampling Schedule | Cell Count | 3 samples/week | 3 samples/week for G/T phase; 1 sample/week for H phase |
| | Metabolites | 3 samples/week | 3 samples/week |
| | BGA (pH, $pCO_2$, $pO_2$) | 3 samples/week | 3 samples/week |
| | Productivity | 3 samples/week | 3 samples/week | critical parameter during the growth and transition phase in each cell culture process run, as the initiation of the transition phase is based on cell concentration. However, in order to reduce cell loss, the frequency of sampling used to determine viable cell density during the harvest phase for the shake tube cell culture process runs was dramatically reduced. Other culture characteristics, such as metabolic profiles of the spent media and productivity can be relied upon to monitor the culture performance in each cell culture process run. The consumption rates of glucose and glutamine, as well as production rates of lactate and glutamate in each cell culture process run were calculated using Equations 1-4 (below). Titer samples were collected and stored at −20° C. until the assay was performed to measure the recombinant human α-galactosidase activity. Cumulative volumetric productivity was calculated using Equation 5 (below). One full cell culture process run was performed with a triplicate set of shake tubes and shake flasks (conditions described below) for each condition. The average and standard deviation of the data were calculated, and are shown in each of FIGS. 1-9.

$$Gluc_{cons} = ([Gluc]_m - [Gluc]_c) * PR \quad \text{Equation 1}$$

$$Lac_{prod} = [Lac]_c * PR \quad \text{Equation 2}$$

$$Gln_{cons} = ([Gln]_m - [Gln]_c) * PR \quad \text{Equation 3}$$

$$Glu_{cons} = ([Glu]_c - [Glu]_m) * PR \quad \text{Equation 4}$$

$$\Sigma VPR = \Sigma(titer * PR) \quad \text{Equation 5}$$

$Gluc_m$: Glucose concentration in fresh media (4.5 g/L)
$Gluc_c$: Glucose concentration in spent media (g/L)
$Lac_c$: Lactate concentration in spent media (g/L)
$Gln_m$: Glutamine concentration in fresh media (4 mM)
$Gln_c$: Glutamine concentration in spent media (mM)
$Glu_m$: Glutamate concentration in fresh media (0.8 mM)
$Glu_c$: Glutamate concentration in spent media (mM)
PR: Perfusion rate per day (re-feed rate)
Titer: rhα-Gal activity (U/L)
VPR: Volumetric productivity (U/L/d)

Results

Growth, Transition, and Early Harvest Phase

Culture performance during the growth phase through transition phase is important to a successful cell culture process run. Table 2 provides a summary of growth/transition parameters of all the cell culture process runs tested. Shake tube cell culture process runs performed using a shaking speed of 140 RPM reached the target transition cell density of 2.86×10⁶ cells/mL on the seventh day of the growth phase. Using this specific throw (orbit) diameter and shake tube, the rotary agitation rate of 160 RPM did not support cell growth and this cell culture process run was terminated in early growth phase. This may be due to the high shear stress the culture was experiencing using this specific combination of shaking speed, throw (orbit) diameter, and shake tube. The shake tube cell culture process runs performed using an agitation frequency of 120 RPM were forced into the transition phase on the ninth day of the growth phase, with a transition cell density of 1.12×10⁶ cells/mL (a density that is outside of the exemplary target transition cell density range of 2-3×10⁶ cells/mL). Visual inspection of the cell culture process runs performed at a frequency of agitation of 120 RPM revealed clumping of the microcarrier cell aggregates, mostly likely due to the inadequate shaking speed.

The viable cell density (Xv) profiles for each cell culture process run is shown in FIG. 1. Due to the low transition density for the shake tube cell culture process runs performed using an agitation frequency of 120 RPM, the viable cell density in these cell culture process runs was not able to recover from the serum washout and decrease in culture temperature that occurs during the transition phase. These cell culture process runs were terminated on harvest day 12. The shake tube cell culture process runs performed using an agitation frequency of 140 RPM (FIG. 1) were able to successfully complete the transition phase and maintain a steady viable cell density profile similar to that of the control shake flask cell culture process runs through transition phase and early harvest phase.

TABLE 2

Summary of Growth Phase Duration and Transition Density of the Cell Culture Process Runs

| Experimental Condition | Transition Density | Growth Day to Transition |
|---|---|---|
| Shake Tube 120 RPM | 1.12 E6 cells/mL | G9 |
| Shake Tube 140 RPM | 2.86 E6 cells/mL | G7 |
| Shake Tube 160 RPM | Terminated due to low cell growth | |
| Shake Flasks | 2.48 E6 cells/mL | G9 |

Culture Growth

The growth and performance of each cell culture process run was monitored. Culture growth for the shake tube cell culture process runs performed using an agitation frequency of 140 RPM, as represented by viable cell concentration (FIG. 1), showed a consistent increase in cell concentration through growth phase and early transition phase to reach a maximum of approximately 2.5-3×10⁶ viable cells/mL. As these cultures were adapting to serum-free medium (beginning in transition phase and through harvest phase), there was a dramatic decrease in viable cell concentration during the early harvest phase. The cultures then stabilized between 0.5-1×10⁶ viable cells/mL throughout the harvest phase of the cell culture process runs. The growth profiles of the shake tube cell culture process runs performed using an agitation frequency of 140 RPM and the shake flask cell culture process runs were comparable throughout the culture period.

Culture Productivity

Culture productivity was monitored throughout the culture period to compare the performance of the shake tube cell culture process runs performed using an agitation frequency of 140 RPM and the shake flask cell culture process runs. The culture productivity for both the shake tube cell culture process runs and the shake flask cell culture process runs peaked at late transition phase/early harvest phase. However, as the cultures were adapting to serum-free medium, a sharp decline in productivity was observed. The cultures recovered from this trough period in early harvest phase, and stabilized through the end of cell culture process runs. When comparing the productivity profile of the shake tube cell culture process runs performed at an agitation frequency of 140 RPM to the shake flask cell culture process runs, a difference was observed during the mid-harvest phase. The shake tube cell culture process runs performed using an agitation frequency of 140 RPM were able to produce a second productivity peak during the mid-harvest phase (H15 to H35). This second peak of productivity was also reflected in the cumulative volumetric productivity profile for these cultures (see, FIG. 3). Historical results from previous shake flask cell culture process runs show that productivity was maintained at a steady level (600 U/L) from mid-harvest phase to end of each cell culture process run. An increase in viable cell concentration was not observed for the shake tube cell culture process runs performed using an agitation frequency of 140 RPM during the mid-harvest phase, which indicated that the productivity peak was a result of an increase in specific cell productivity.

Culture Metabolism

Figure 4:
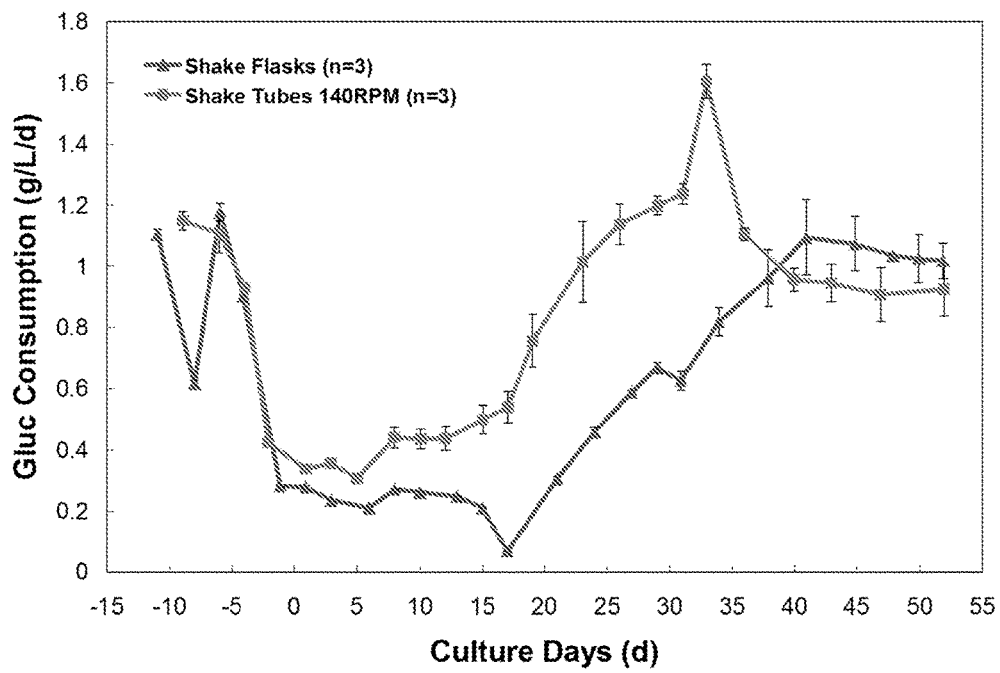
FIG. 4 is a graph of the glucose consumption rate (grams of glucose/L/day) over time in shake tube cell culture process runs performed using an agitation frequency of 140 RPM (n=3) and in shake flask cell culture process runs (n=3). The mean of the data±standard deviation are shown.
Figure 5:
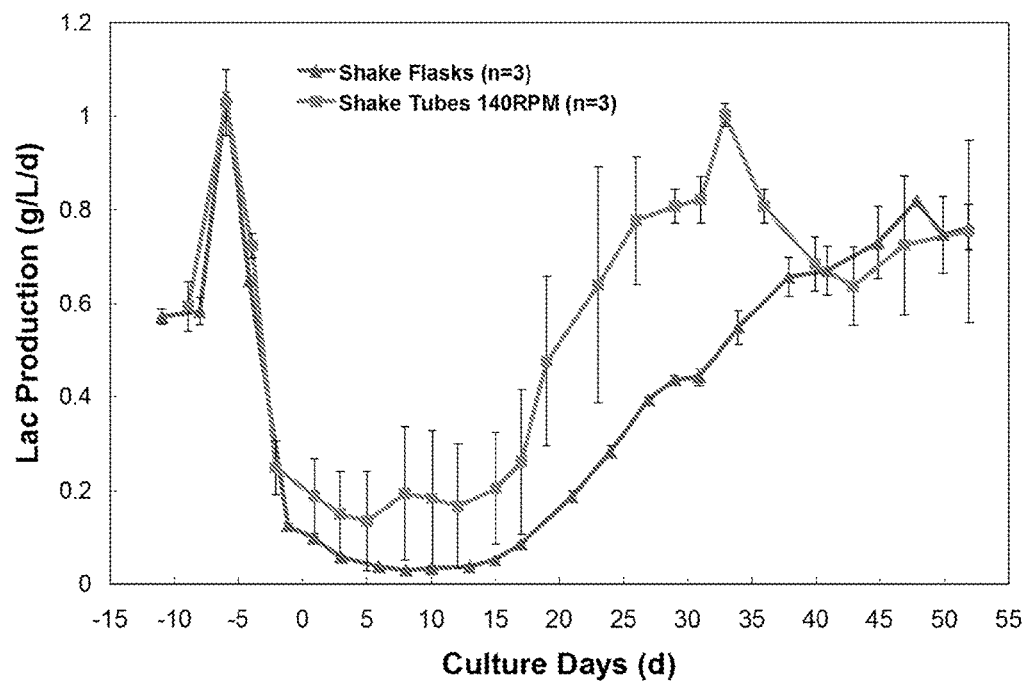
FIG. 5 is a graph of the lactate production rate (grams of lactate/L/day) over time in shake tube cell culture process runs performed using an agitation frequency of 140 RPM (n=3) and in shake flask cell culture process runs (n=3). The mean of the data±standard deviation are shown.
Figure 6:
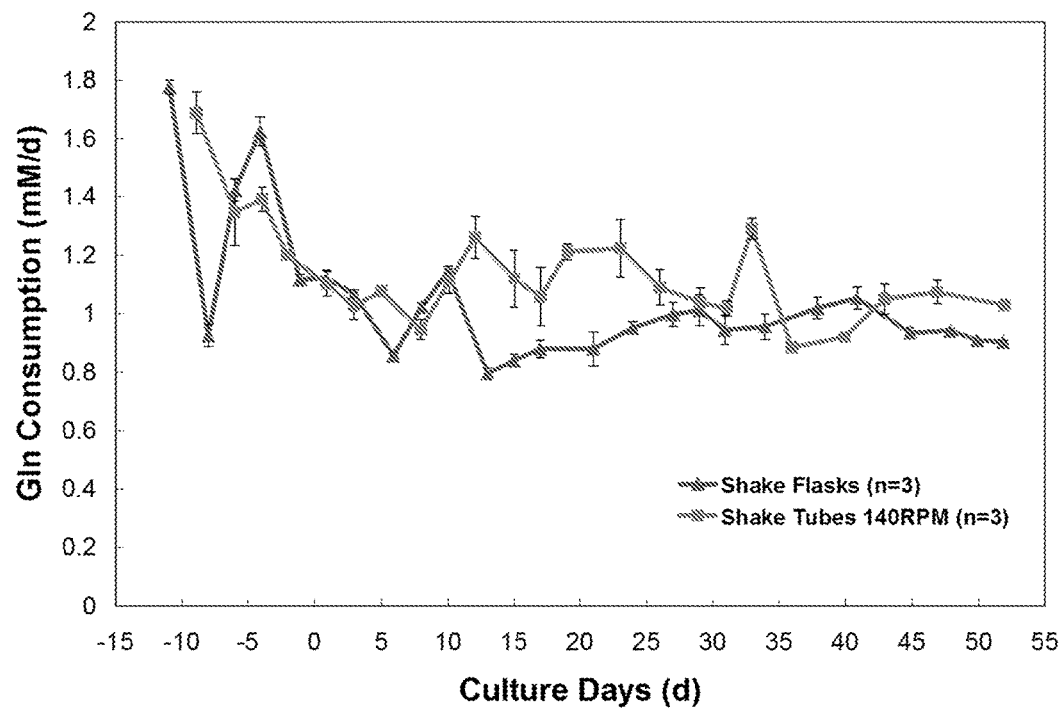
FIG. 6 is a graph of the glutamine consumption rate (mM/day) over time in shake tube cell culture process runs performed using an agitation frequency of 140 RPM (n=3) and in shake flask cell culture process runs (n=3). The mean of the data±standard deviation are shown.
Figure 7:
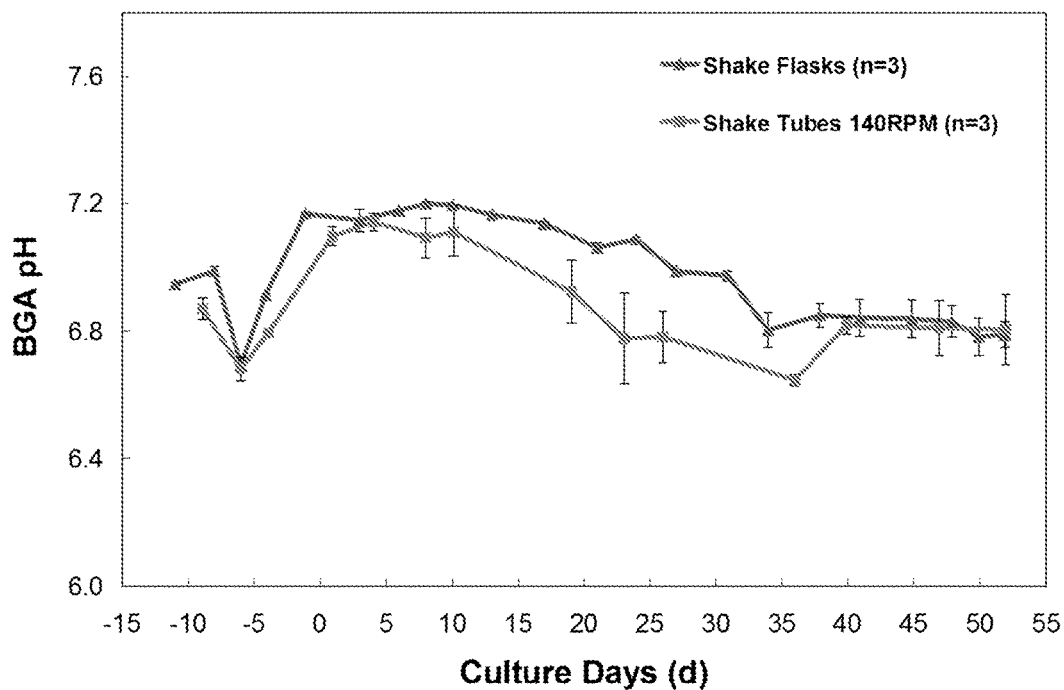
FIG. 7 is a graph of the pH over time in shake tube cell culture process runs performed using an agitation frequency of 140 RPM (n=3) and in shake flask cell culture process runs (n=3). The mean of the data±standard deviation are shown.
Figure 8:
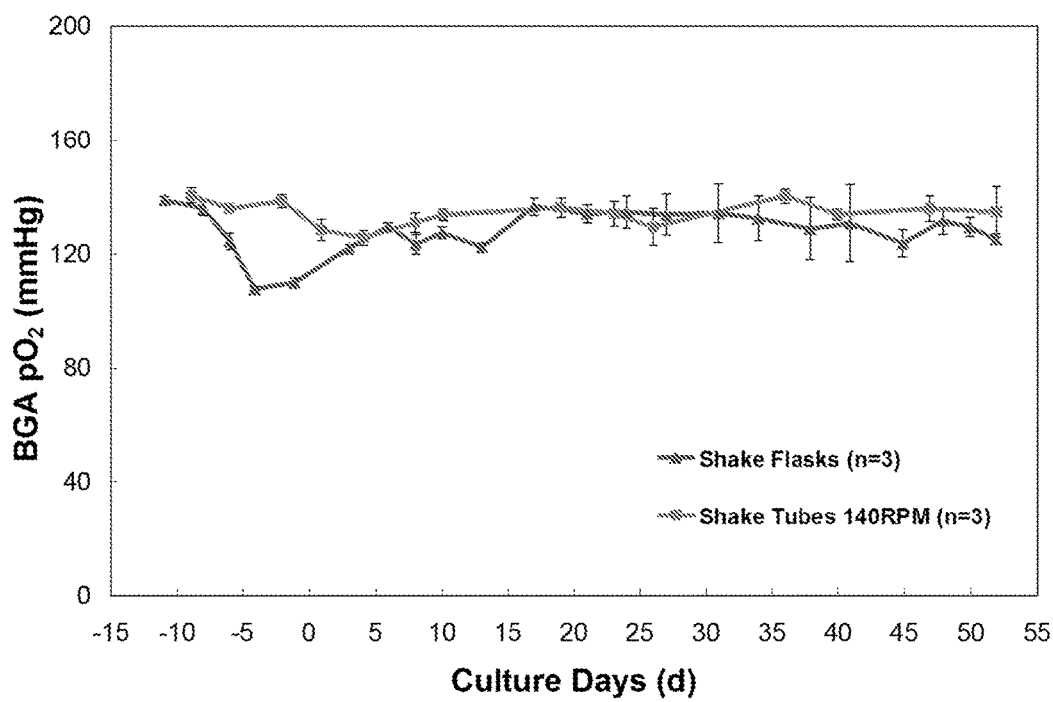
FIG. 8 is a graph of the partial pressure of $O_2$ ($pO_2$) (mmHg) over time in shake tube cell culture process runs performed using an agitation frequency of 140 RPM (n=3) and in shake flask cell culture process runs (n=3). The mean of the data±standard deviation are shown.
Figure 9:
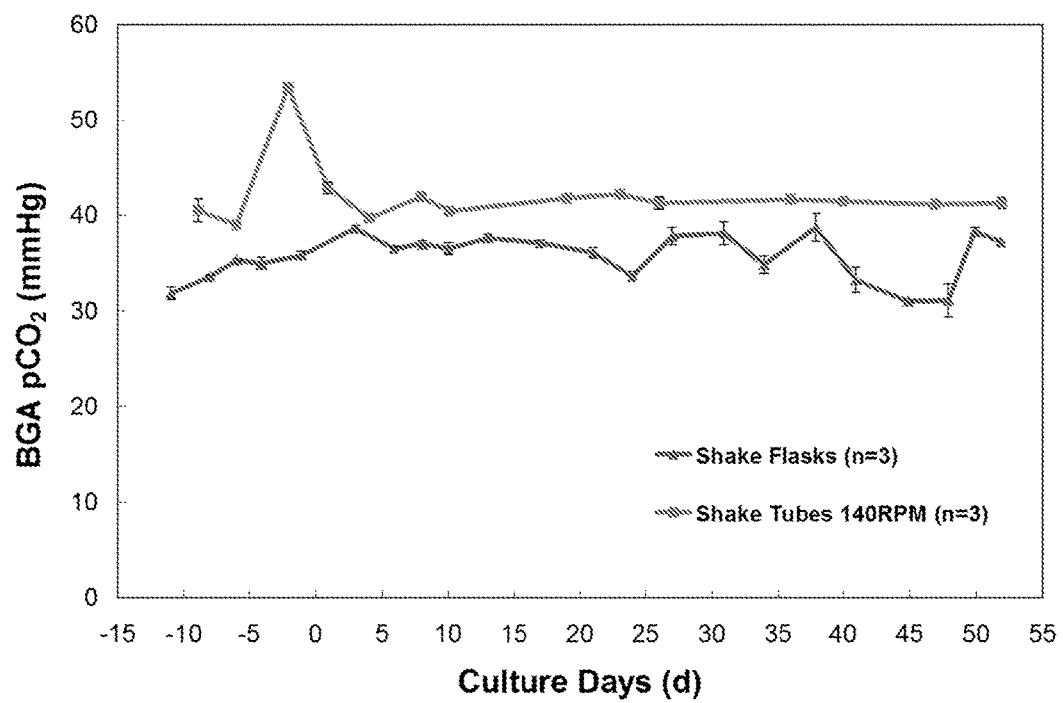
FIG. 9 is a graph of the partial pressure of $CO_2$ ($pCO_2$) (mmHg) over time in shake tube cell culture process runs performed using an agitation frequency of 140 RPM (n=3) and in shake flask cell culture process runs (n=3). The mean of the data±standard deviation are shown.

Cellular metabolism was monitored in each cell culture process run through the measurement of the glucose, lactate, glutamine, and glutamate concentrations in the spent media. The glucose consumption rate (FIG. 4) and lactate production rate (FIG. 5) were calculated from the glucose and lactate concentration present in the spent media and feed media samples. Overall, both glucose consumption and lactate production corroborated with the cell growth profile in each cell culture process run (FIG. 1). The most dynamic periods of the culture occurred at two different culture stages: i) where cell proliferation occurred in the growth phase (with the serum-containing medium), and ii) mid- to late-harvest phase, when a re-growth period occurred, and an increase in both viable cell density and metabolic activity were observed. Slightly higher glucose consumption rate and lactate production rate were observed in the shake tube cell culture process runs performed using an agitation frequency of 140 RPM when compared to the shake flask cell culture process runs during mid-harvest phase (FIGS. 4 and 5). This was also when the shake tube cell culture process runs performed using an agitation frequency of 140 RPM showed a higher productivity than the shake flask cell culture process runs. Comparable trends for glutamine consumption rate (FIG. 6) and glutamate production rate were observed for the shake tube shake tube cell culture process runs performed using an agitation frequency of 140 RPM and the shake flask cell culture process runs.

Culture pH, pCO$_2$, and pO$_2$

Culture pH, pCO$_2$, and pO$_2$ profiles were monitored in each cell culture process run using a blood gas analyzer (BGA) during sampling. The shake tube cell culture process runs performed using an agitation frequency of 140 RPM and the shake flasks cell culture process runs had comparable pH, pCO$_2$, and pO$_2$ profiles (FIGS. 7-9) over most of the duration of the process runs. The pH profiles (FIG. 7) corroborated with the viable cell concentration dip that occurs in both the shake tube cell culture process runs performed using an agitation frequency of 140 RPM and the shake flask cell culture process runs during the transition period. The pCO$_2$ profiles (FIG. 9) show that a level of pCO$_2$ between 30-40 mmHg was maintained in each cell culture process run, which correlates to the 5% CO$_2$ setting of the incubator.

In sum, the exemplary batch re-feed shake tube culture model described in this Example was demonstrated to be an acceptable model for the large-scale production of recombinant human alpha-galactosidase using a 2000-L bioreactor. The exemplary shake tube cell culture process run described in the Example demonstrated similar cell growth and productivity to that of a shake flask cell culture process run that was previously demonstrated to be an acceptable model for the large-scale production of recombinant human alpha-galactosidase using a 2000-L bioreactor.

Under the present experimental conditions (e.g., use of a specific throw (orbit) diameter), agitation of the shake tube cultures at a frequency of 140 RPM was shown to achieve a target transition cell density of 2-3×10$^6$ cells/mL (a cell density of 2.86×10$^6$ cells/mL achieved on the seventh day of the growth phase), and to maintain a growth profile similar to that achieved using the control shake flask cell culture process runs. Unlike the shake flask cell culture process runs, the shake tube cell culture process runs performed using an agitation frequency of 140 RPM were able to produce a second productivity peak during the mid-harvest phase. As an increase in viable cell density was not observed during this period in the shake tube cell culture process runs, the increase in productivity is attributed to an increase in specific cell productivity. The changes in the culture metabolism are consistent with these findings—with both the glucose consumption and lactate production during the mid-harvest phase measured to be higher in the shake tube cell culture process runs performed using an agitation frequency of 140 RPM than in the shake flask cell culture process runs. Other metrics, such as culture pH, pCO$_2$, and pO$_2$, were found to be similar between the shake tube cell culture process runs performed using an agitation frequency of 140 RPM and the shake flask cell culture process runs.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of culturing an adherent Chinese hamster ovary (CHO) cell, the method comprising:
   providing a conical shake tube containing an adherent CHO cell disposed in a first liquid culture medium, wherein the first liquid culture medium occupies about 10% to about 30% of the volume of the conical shake tube and contains a plurality of microcarriers at a concentration of about 1.0 g/L to about 15.0 g/L, wherein the microcarriers have (1) an average diameter of about 200 Tm to about 300 Tm and (2) a plurality of pores, wherein the plurality of pores have an average diameter of about 25 µm to about 35 µm;
   incubating the conical shake tube for a period of time at about 32° C. to about 39° C. with a rotary agitation of about 130 revolutions per minute (RPM) to about 150 RPM; and
   after about the first 48 to 96 hours of the period of time, continuously or periodically removing a first volume of the first liquid culture medium and adding to the first liquid culture medium a second volume of a second liquid culture medium, wherein the first and second volumes are about equal, and the method achieves a viable cell density of greater than 2.0×10$^6$ cells/mL in the first liquid culture medium or a combination of the first and second liquid culture medium at some point during the period of time.

2. The method of claim 1, wherein the adherent CHO cell contains a nucleic acid encoding a recombinant protein.

3. The method of claim 2, further comprising:
   recovering the recombinant protein from the adherent CHO cell or from the first and/or second liquid culture medium.

4. The method of claim 2, further comprising:
   detecting the recombinant protein in the adherent CHO cell or in the first and/or second culture medium; and
   comparing the amount of recombinant protein present in the adherent CHO cell or in the first and/or second culture medium to a reference level of recombinant protein.

5. The method of claim 4, wherein the reference level of recombinant protein is a level of recombinant protein produced using a different culturing method.

6. The method of claim 2, further comprising:
detecting the recombinant protein in the adherent CHO cell or in the first and/or second culture medium;
comparing the amount of recombinant protein present in the adherent CHO cell or in the first and/or second culture medium to a reference level of recombinant protein produced by a different method that uses one or more of a different first or second liquid culture medium, a different raw ingredient or supplement present in the first or second liquid culture medium, or a different source of an adherent CHO cell; and
identifying the first or second liquid culture medium, the raw ingredient or supplement present in the first or second liquid culture medium, or the source of the adherent CHO cell that is associated with an increased amount of recombinant protein as compared to the reference level as being efficacious for use in a method of producing a recombinant protein.

7. The method of claim 2, further comprising:
detecting the recombinant protein in the adherent CHO cell or in the first and/or second culture medium;
comparing the amount of recombinant protein present in the adherent CHO cell or in the first and/or second culture medium to a reference level of recombinant protein produced by a different method; and
identifying and removing or altering in a manufacturing process any culture components or parameters that are associated with a decrease in the amount of recombinant protein produced as compared to the reference level, or identifying and adding to a manufacturing process any culture components or parameters that are associated with an increase in the amount of recombinant protein produced as compared to the reference level.

8. The method of claim 1, wherein the removing of the first volume of the first liquid culture medium and the adding of the second volume of the second liquid culture medium is performed periodically.

9. The method of claim 1, wherein the first volume of the first liquid culture medium removed and the second volume of the second liquid culture medium added are increased over time.

10. The method of claim 1, wherein:
the conical shake tube has a volume of between about 10 mL to about 100 mL; or
the adherent CHO cell is suspended in about 2 mL to about 20 mL of the first liquid culture medium.

11. The method of claim 1, wherein after about the first 48 to 96 hours of the period of time, in each 24-hour period, the first volume of the first liquid culture medium removed and the second volume of the second liquid culture medium added is about 30% to about 95% of the volume of the first liquid culture medium.

12. The method of claim 1, wherein the conical shake tube is incubated at a reactor angle of about 25 degrees to about 90 degrees from horizontal.

13. The method of claim 1, wherein the plurality of microcarriers are at a final concentration of about 1.0 g/L to about 2.0 g/L in the conical shake tube.

14. A method of culturing an adherent CHO cell, the method comprising:
(a) providing a conical shake tube containing an adherent CHO cell disposed in a first liquid culture medium that occupies about 10% to about 30% of the volume of the conical shake tube and contains a plurality of microcarriers in a concentration of about 1.0 g/L to about 15.0 g/L, wherein the microcarriers have (1) an average diameter of about 200 Tm to about 300 Tm and (2) a plurality of pores, wherein the plurality of pores have an average diameter of about 25 µm to about 35 µm;
(b) incubating the conical shake tube for a first time period at about 35° C. to about 39° C. with a rotary agitation of about 130 revolutions per minute (RPM) to about 150 RPM, and after about the first 48 to 96 hours of the first period of time, in each subsequent 24-hour period,
(i) continuously or periodically removing a first volume of the first liquid culture medium that is substantially free of microcarriers from the conical shake tube, wherein the first volume is about 10% to about 95% of the volume of the first liquid culture medium; and
(ii) adding to the conical shake tube a second volume of a second liquid culture medium, wherein the first and second volumes are about equal;
(c) incubating the conical shake tube after the cell concentration reaches about target cell density for a second time period of about 2 days to about 7 days, at about 32° C. to about 39° C. with the rotary agitation, and in each 24-hour period, performing steps (b)(i) and (b)(ii), wherein the first and second liquid culture media used in step (b) are of a substantially different type from those used in step (c); and
(d) incubating the conical shake tube for a third time period greater than 2 days, at about 35° C. to about 39° C. with the rotary agitation, and in each 24-hour period, performing steps (b)(i) and (b)(ii), wherein the first and second liquid culture media used in step (c) are of the same type as those used in step (d).

15. The method of claim 14, wherein the adherent CHO cell contains a nucleic acid encoding a recombinant protein.

16. The method of claim 15, further comprising:
(e) recovering the recombinant protein from the adherent CHO cell or the first and/or second liquid culture medium used during the first, second, and/or third period of time.

17. The method of claim 14, wherein the removing of the first volume of the first liquid culture medium, and the adding of the second volume of the second liquid culture medium in one of more of the first time period, the second time period, and the third time period is performed periodically.

18. The method of claim 14, wherein:
the shake tube has a volume of between about 10 mL to about 100 mL; or
the volume of the first culture medium is about 2 mL to about 20 mL.

19. The method of claim 14, wherein the first volume of the first liquid culture medium removed and the second volume of the second liquid culture medium added in one or more of the first time period, the second time period, and the third time period is about 70% of the volume of the first liquid culture medium.

20. The method of claim 14, wherein the conical shake tube is incubated in (b), (c), and (d) at a reactor angle of about 25 degrees to about 90 degrees from horizontal.

21. A method of testing for the presence of a contaminant in a first or second liquid culture medium, a raw material used to generate a first or second liquid culture medium, or a source of an adherent CHO cell, the method comprising:
providing a conical shake tube containing an adherent CHO cell disposed in a first liquid culture medium, wherein the first liquid culture medium occupies about 10% to about 30% of the volume of the conical shake tube and contains a plurality of microcarriers at a concentration of about 1.0 g/L to about 15.0 g/L, wherein the microcarriers have (1) an average diameter of about 200 Tm to about 300 Tm and (2) a plurality of pores, wherein the plurality of pores have an average diameter of about 25 µm to about 35 µm;

incubating the conical shake tube for a period of time at about 32° C. to about 39° C. and with a rotary agitation of about 130 revolutions per minute (RPM) to about 150 RPM; and after about the first 48 to 96 hours of the period of time, continuously or periodically removing a first volume of the first liquid culture medium and adding to the first liquid culture medium a second volume of a second liquid culture medium, wherein the first and second volumes are about equal;

detecting the recombinant protein in the adherent CHO cell or in the first and/or second culture medium;

comparing the amount of recombinant protein present in the adherent CHO cell or in the first and/or second culture medium to a reference level of recombinant protein produced by a different method that uses one or more of a different first or second liquid culture medium, a different raw material to generate the first or second liquid culture medium, or a different source of the adherent CHO cell; and identifying the first or second liquid culture medium, the raw material used to generate the first or second liquid culture medium, or the source of an adherent CHO cell as containing a contaminant when the level of recombinant protein produced is less than the reference level.

* * * * *